US006376664B1

(12) United States Patent  (10) Patent No.: US 6,376,664 B1
Chan et al.  (45) Date of Patent: Apr. 23, 2002

(54) CYCLIC BIS-BENZIMIDAZOLE LIGANDS AND METAL COMPLEXES THEREOF

(75) Inventors: Michael K. Chan, Hilliard, OH (US); Wai H. Kwok, Kowloon (KR); Huichang Zhang, Charlottesville, VA (US); Maosheng Duan, Cary, NC (US)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 09/528,273

(22) Filed: Mar. 17, 2000

Related U.S. Application Data
(60) Provisional application No. 60/124,906, filed on Mar. 17, 1999.

(51) Int. Cl.[7] ............ C07D 225/00; C07D 245/00; C07D 487/00; C07D 401/00
(52) U.S. Cl. ............ 540/465; 540/472; 540/476; 546/273.1
(58) Field of Search .............. 540/465, 472, 540/476, 461, 121, 145; 424/9.3, 9.361, 9.362, 9.61; 546/273.1; 534/15, 16

(56) References Cited

U.S. PATENT DOCUMENTS

| | | | |
|---|---|---|---|
| 3,481,945 A | * 12/1969 | Nichols et al. | 540/472 |
| 5,180,821 A | * 1/1993 | Obermayer et al. | 540/465 |
| 5,674,467 A | * 10/1997 | Maier et al. | 424/1.65 |
| 5,925,744 A | * 6/1999 | Haner et al. | 534/15 |

OTHER PUBLICATIONS

"Synthesis and Characterization of the Dimethyl–Substituted Bisbenzimidazole Ligand and Its Manganese Complex" by Kwok, et al., *Inorg. Chem.*, 2000, 39, 2367–2376.
"Structural Trends in First–Row Transition–Metal Bis(benzimikazole) Complexes" by Payra, et al.,*Inorg. Chem.* 2000, 39, 1076–1080.

* cited by examiner

*Primary Examiner*—Michael G. Hartley
(74) *Attorney, Agent, or Firm*—Calfee, Halter & Griswold LLP

(57) ABSTRACT

Cyclic bis benzimidazole ligands of the following formula are formed by contacting a (2-aminophenyl)-benzimidazole-4-carboxaldehyde ethylene acetal or a (2-nitrophenyl)-benzimidazole-4-benzaldehyde with an acid optionally in the presence of a metal or a metal salt.

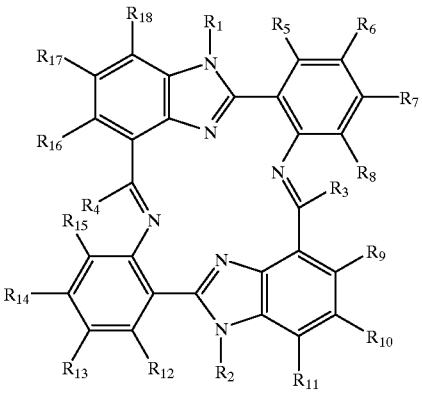

wherein
$R_1$ and $R_2$ may be the same or different and are selected from H, an alkyl having 1 to 10 carbon atoms, a benzyl group, a substituted 2-ethylphenyl group, a carbonyl group, a phenyl substituent, a tosyl group, and an alkylsulfonate group;

$R_3$ and $R_4$ may be the same or different and are selected from H, methyl, and ethyl; and $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ may be the same or different and are selected from H, alkyl having 1 to 10 carbon atoms, fluoride, chloride, bromide, iodide, nitro, amino, a carboxylate, an ester, and a phenyl group.

27 Claims, 14 Drawing Sheets

Porphyrins

Phthalocyanines

Bis-benzimidazoles

Porphyrins

Phthalocyanines

Bis-benzimidazoles

CYCLIC BIS-BENZIMIDAZOLE LIGANDS AND METAL COMPLEXES THEREOF

CROSS-REFERENCE TO RELATED APPLICATION

This application is based on provisional application Ser. No. 60/124,906, filed Mar. 17, 1999, the benefit of which is hereby claimed.

BACKGROUND OF THE INVENTION

Naturally-occurring metallotetrapyrroles such as, for example, metalloporphyrins and other related metallotetrapyrroles (corrins, F430) are important cofactors in biology, where they serve as sensors,[1-5] transporters,[6,7] and catalysts.[8-14] Synthetic metallotetrapyrroles have also found numerous industrial applications, including the catalytic oxidation of organic substrates[15-19] and the fabrication of novel materials.[20-22] In light of their general importance and extensive applicability, it is desirable to have new compounds which are similar in structure and function to the tetrapyrrole ligands and metallotetrapyrroles, but which also have different structural features that are advantageous.

SUMMARY OF THE INVENTION

In accordance with the present invention, new compounds which are similar and function to tetrapyrrole ligands are provided. The new compounds are designated herein as "cyclic bis benzimidazole ligands". One group of cyclic bis-benzimidazole (BBZ) ligands have the following formula:

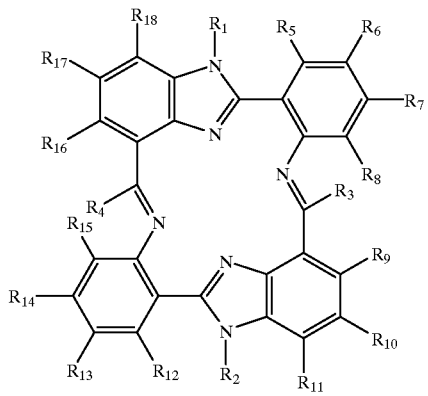

$R_1$ and $R_2$ may be the same or different;

$R_1$ and $R_2$ are selected from the group consisting of H, an alkyl having 1 to 10 carbon atoms, a benzyl group, a substituted 2-ethylphenyl group, a carbonyl group, a phenyl substituent, a tosyl group, and an alkylsulfonate group;

$R_3$ and $R_4$ may be the same or different;

$R_3$ and $R_4$ are selected from the group consisting of H, a methyl, and an ethyl;

$R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ may be the same or different; and $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ are selected from the group consisting of H, an alkyl having 1 to 10 carbon atoms, fluoride, chloride, bromide, iodide, nitro, amino, a carboxylate, an ester, and a phenyl group.

Preferably, the BBZ ligand is an unsubstituted, a methyl substituted, or a benzyl substituted bis benzimidazole ligand.

The unsubstituted BBZ ligand is shown below:

Unsubstituted

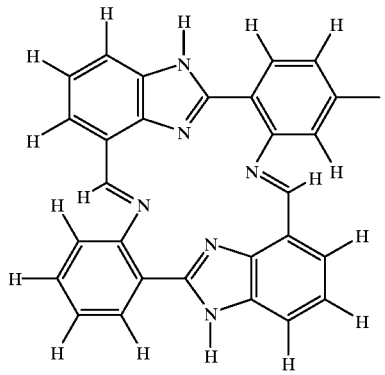

The methyl substituted BBZ ligand is shown below:

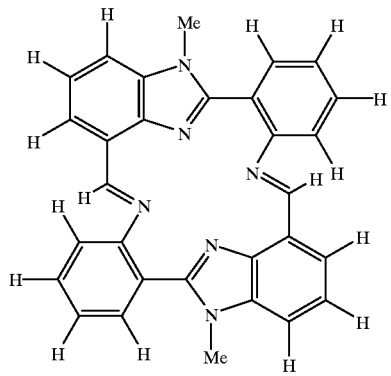

The benzyl substituted BBZ ligand is shown below:

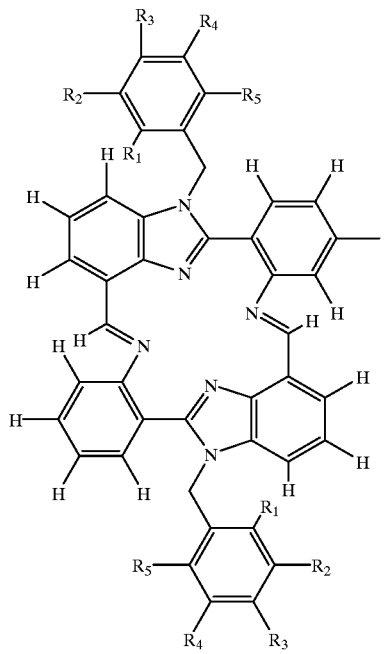

where $R_{1'}$, $R_{2''}$, $R_{3'}$, $R_{4'}$, and $R_{5'}$, are the same or different and $R_{1'}$, $R_{2'}$, $R_{3'}$, $R_{4'}$, and $R_{5'}$, are elected from the group consisting of H, an alkyl having 1 to 10 carbon atoms, fluoride, chloride, bromide, iodide, nitro, amino, a carboxylate, an ester, and a phenyl group.

Another group of the cyclic BBZ ligands, the reduced BBZ ligands, have the following formula

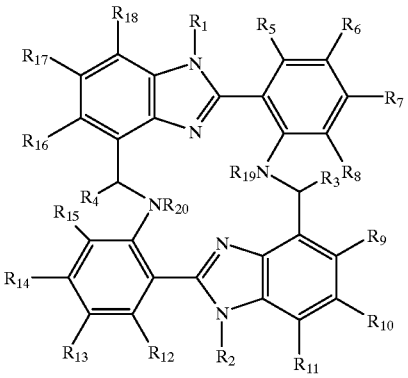

where $R_1$ and $R_2$ may be the same or different;

$R_1$ and $R_2$ are selected from the group consisting of H, an alkyl having 1 to 10 carbon atoms, a benzyl group, a substituted 2-ethylphenyl group, a carbonyl group, a phenyl substituent, a tosyl group, and an alkylsulfonate group;

$R_3$ and $R_2$ may be the same or different;

$R_3$ and $R_4$ are selected from the group consisting of H, a methyl, and an ethyl;

$R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ may be the same or different;

$R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ are selected from the group consisting of H, an alkyl having 1 to 10 carbon atoms, fluoride, chloride, bromide, iodide, nitro, amino, a carboxylate, an ester, and a phenyl group;

$R_{19}$ and $R_{20}$ are the same or different: and $R_{19}$ and $R_{20}$ are selected from the group consisting of H, an alkyl having 1 to 10 carbon atoms, and a benzyl derivative.

These bis-benzimidazoles, in a manner similar to phthalocyanines, are useful as non-linear optical materials for use in information processing, optical switching, optical frequency conversion and telecommunications. For example, various BBZ ligands and metal complexes are useful as optical switches in fiber-optic networks or other photonic devices. The bis-benzimidazole ligands may also serve as monomeric units in organic polymers that are used in electrochemical devices such as batteries, and amperometric sensors. The bis-benzimidazole ligands are also useful as monomeric units in the backbone of polymers which are used in optical devices such as optical sensors and optical data storage devices. Chiral bis-benzimidazole ligands are useful as an affinity ligand for chiral separations.

In the metal complexes made in accordance with the present invention, a metal ion is complexed to the two benzimidazole nitrogens as well as the two schiff base/or amine nitrogens of the BBZ ligand. Essentially any mono-, di- or trivalent metal can be used for this purpose. For example, Na, K, Ru, Cs, Ca, Mg, Ba, Sr, Fe, Co, Ni, Cu, Mn, Ga, Si, Ge, Sn and Sb can be used. Preferably the metal ion is a transition metal ion, more preferably iron or manganese.

The bis-benzimidazole metal complexes are catalysts useful in many organic reactions such as, for example, the epoxidation of olefins, the polymerization of olefins, atom transfer reactions and hydrogenation reaction.

The present invention also relates to methods of making the bis-benzimidazole ligands and the metal complexes thereof. These methods involve cyclizing a 2-amino or 2-nitro phenyl-benzimidazole substituted at its 4 position with an acetal or aldehyde moiety by contact with an acid. If a metal ion is present during cyclization, the ligand will coordinate around the metal ion as it forms through cyclization. If a metal ion is not present, cyclization will nonetheless occur with the benzimidazole nitrogens becoming protonated. In either case, a stable cyclic bis-benzimidazole ligand will form.

Particular methods for preparing the bis-benzimidazole involve coupling an unsubstituted or substituted phenylenediamine precursor with a substituted phenylcarboxaldehyde, or an unsubstituted phenylcarboxaldehyde, or an aldehyde. Preferably, the coupling is achieved using copper acetates as a catalyst. One method comprises the following steps: (1) reducing the benzothiadiazole group of a phenylenediamine precursor to the deprotect the diamine, (2) coupling of the phenyl diamine with an aldehyde to form a benzimidazole group, preferably via copper catalysis (3) oxidizing the benzyl alcohol group to a carboxaldehyde (4) protecting the carboxaldehyde with ethylene glycol, (5) alkylating/substituting the benzimidazole nitrogen, (6) reducing the nitro group to the amine, and (7) deprotecting the aldehyde and cyclizing under acidic conditions to provide the BBZ ligand. The metal complex is formed by refluxing the desired metal with the BBZ ligand.

A second method for forming the BBZ ligand comprises the following steps (1) coupling of a phenyl diamine with an aldehyde to form a benzimidazole group, preferably via copper catalysis (2) alkylating/substituting the benzimidazole nitrogen, (3) dibrominating the methyl group on the phenyl ring, (4) converting the dibromide to a carboxaldehyde and (5) metal/acid catalyzed reducing the nitro group and cyclizing. A third method for forming the BBZ ligand comprises the following steps (1) coupling a phenyl diamine with an aldehyde to form a benzimidazole group, preferably via copper catalysis (2) alkylating/substituting the benzimidazole nitrogen, (3) oxidation of the aromatic methyl to a carboxaldehyde, and (4) metal/acid catalyzed reduction of the nitro group and cyclizing.

The present invention also relates to method of using a BBZ metal complex to prepare an epoxide. The method comprises contacting an olefin with an oxo transfer agent or oxidant and a BBZ metal complex in a mixture comprising an aqueous or organic substrate to provide an epoxide of the olefin.

DETAILED DESCRIPTION OF THE INVENTION

Figure 1:
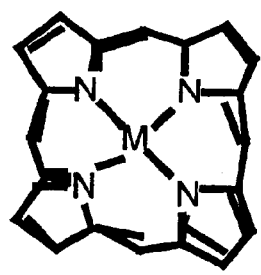
FIG. 1 is a comparison of the structures of porphyrins, phthalocyanines and bis-benzimidazoles.
Figure 1:
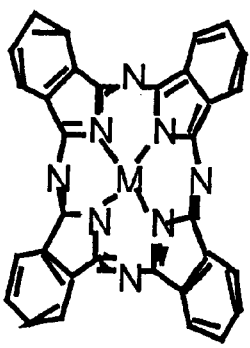
Figure 1:
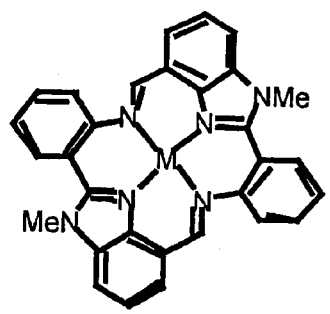

In accordance with the present invention, new classes of cyclic bis benzimidazole (BBZ) ligands are provided. In addition, new classes of complex chemical compounds in which these cyclic bis benzimidazoles are the ligands are also provided.

In accordance with the present invention, it has been found that certain phenyl-substituted benzimidazole compounds when dissolved in polar solvents will cyclize in the presence of another complexing cation to form stable organic ligands. When divalent metal cations (especially the transitions metal cations) are present in the system, two benzimidazole molecules cyclize about each divalent metal cation with the benzimidazole nitrogens of these molecules coordinating about the metal cation. If divalent metal cations are absent, the benzimidazole nitrogens of these new ligands become protonated (or substituted with monovalent metal ions) instead. In either case, stable organic ligands are formed having intrinsic non-planarity with the metal complexes also having significant catalytic activity in various different reactions including epoxidation of styrene, for example.

The particular phenyl-substituted benzimidazole compounds which will undergo this cyclization reaction include the (2-aminophenyl)-benzimidazole-4-carboxaldehyde acetals, especially the (2-aminophenyl)-benzimidazole-4-carboxaldehyde alkyl acetals in which the alkyl group has from 1 to 10 carbon atoms, and particularly the (2-aminophenyl)-benzimidazole-4-carboxaldehyde ethyl acetals. Another type of phenyl-substituted benzimidazole compounds which will undergo this cyclization reaction are the (2-nitrophenyl)-benzimidazole-4-benzaldehydes.

The complex chemical compounds provided by the present invention can be viewed as being represented by the following formula

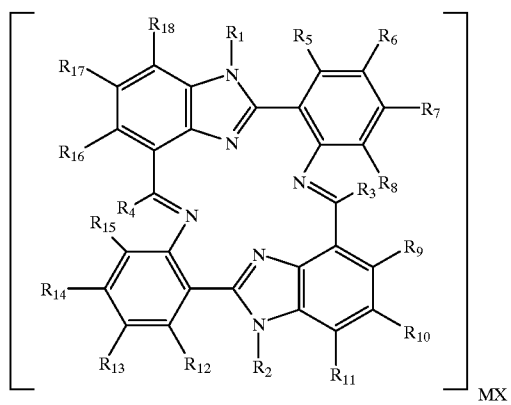

wherein

R$_1$ and R$_2$ may be the same or different and are selected from H, an alkyl having 1 to 10 carbon atoms, a benzyl group, a substituted 2-ethylphenyl group, a carbonyl group, a phenyl substituent, a tosyl group, an alkylsulfonate group and a methyl-2-pyrrolidene methyl group;

R$_3$ and R$_4$ may be the same or different and are selected from H, methyl, and ethyl;

R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, and R$_{18}$ may be the same or different and are selected from H, alkyl having 1 to 10 carbon atoms, fluoride, chloride, bromide, iodide, nitro, amino, a carboxylate, an ester, and a phenyl group;

M represents a counter-cation selected from the group consisting of hydrogen and metals from Groups IA and IIA of the Periodic Table, the transition metals, silicon and lead; and X represents a complexing counter-anion.

Suitable complexing counter-anions include the halide ions, especially chloride, perchlorate and tetraphenyl boride (Ph$_4$B$^-$). Other effective counter-anions include the sulfate, phosphate, carbonate, bicarbonate, tetrafluoroboride (BF$_4^-$) and hexafluorophosphide (BF$_6^-$). Other anions which do not adversely affect the system can also be used.

The new ligands and complexes of the present invention can be made by forming a solution of the benzimidazole compound in a suitable polar solvent and then adding to the system additional compounds for supplying the counter-cation and counter-anion of the target product compound, i.e. the "M" and "X" groups in the above formula.

Essentially any liquid can be used for the polar solvent so long as it is capable of dissolving the benzimidazole compound and its cyclization product, capable of dissociating the M and X groups of the above formula and otherwise does not adversely react with any of the other components in the system. Water and acetonitrile are preferred. Other suitable solvents are methanol, ethanol and the like.

Essentially any compound can be used for supplying the counter-cations and counter-anions of the inventive complexes. Of course, compounds which might adversely react with other components in the system or supply ions not to be included in the target complex should be avoided. Typically, the counter-cation and counter-anion are added in the form of simple salts of one another, although they can be added in metallic form in the presence of an acid. Where the target complex is the protonated form of the compound, a simple acid can be used.

In this connection, it has been further found in accordance with a particular embodiment of the invention that the cyclic bis benzimidazole monomers of the present invention combine in some instances to form a dimerized product composed of two cyclic bis benzimidazole groups bound to one another via a μ-oxo linkage (i.e. M—O—M). In particular, it has been found that when cyclic bis benzimidazoles are made in accordance with the present invention, a dimerized product will form when the counter cation of the complex is multivalent (e.g. Fe, Mn, Cu), provided that dimerized product is formed and/or reacted under oxidizing conditions.

As shown in FIG. 1, cyclic BBZ ligands have the same ring size as porphyrins and phthalocyanines, suggesting that they might exhibit similar metal chelating behavior. They offer, however, potential synthetic advantages toward the preparation of derivatives due to the ease of substitution at the benzimidazole nitrogen.

This macrocycle has the same ring size as a porphyrin or phthalocyanine suggesting that it might exhibit similar metal-chelating behavior. Unlike these classical tetrapyrroles, however, molecular mechanics calculations (HYPERCHEM 4.5, Hypercube Inc.) predict that bis benzimidazole complexes should be inherently nonplanar. In light of the fact that this non-planarity leads to two distinct hands, bis benzimidazole complexes may have potential for promoting the chiral recognition of ligands and substrates. In addition, bis benzimidazole ligands offer potential synthetic advantages over porphyrins. Due to the ease of substitution at the N-3 benzimidazole nitrogen, the preparation of derivatized forms is relatively straightforward.

The present invention also relates to metal complexes of the cyclic BBZ ligands, to methods for making such ligands and complexes, and to methods of using the metal complexes of the cyclic BBZ ligands as catalysts.

Synthesis of the BBZ Ligands and Metal Complexes

Synthetic Scheme 1: [H$_2$(Me$_2$BBZ)]ClO$_4$)$_2$ (8) and [Mn(Me$_2$BBZ)Cl]Cl (9)

Figure 2:
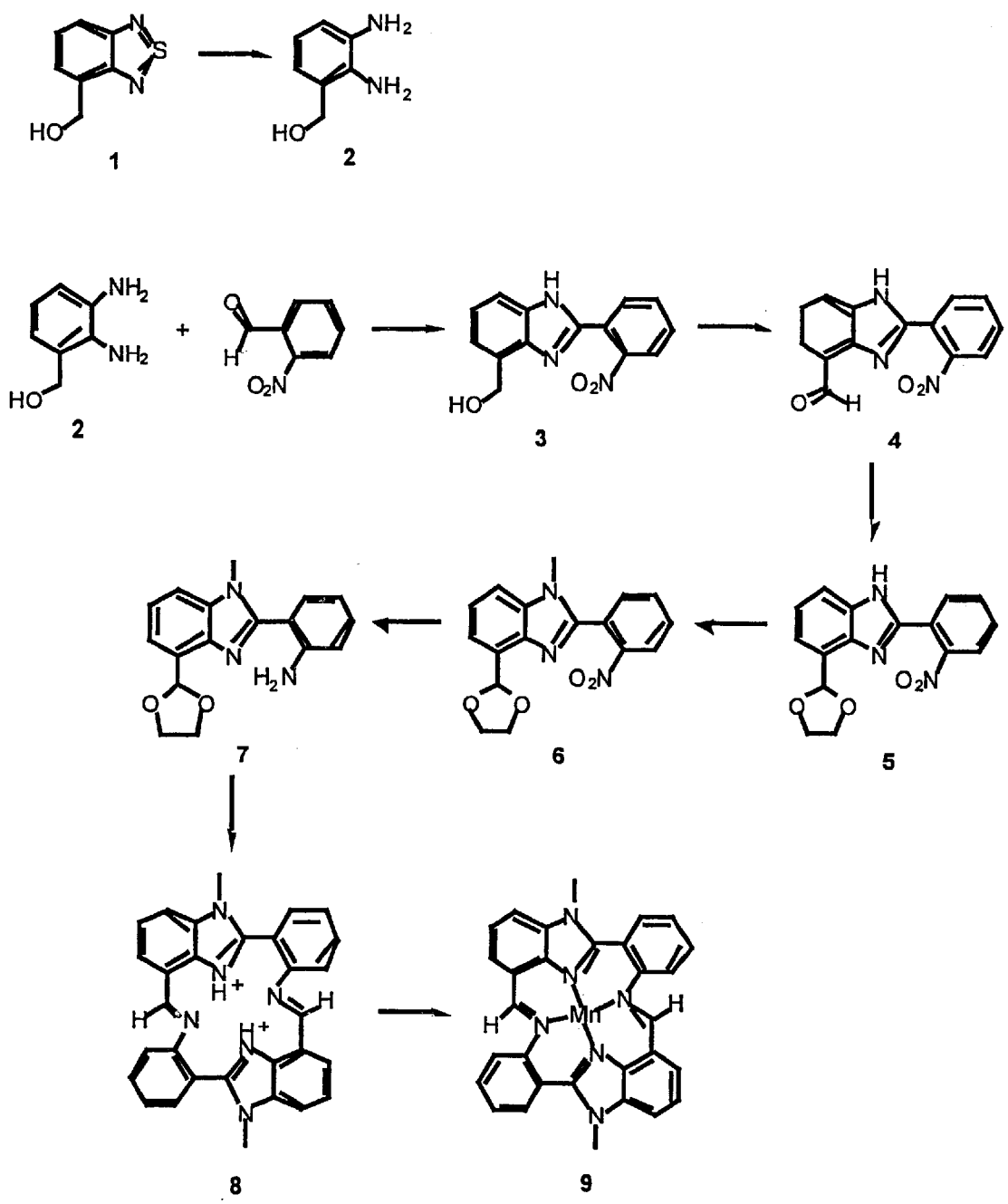
FIG. 2. shows one synthetic scheme for the synthesis of the Me$_2$BBZ ligand and its associated manganese complex.

A procedure for preparing a BBZ ligand and its related metal complex is shown in FIG. 2. The precursor, 4-hydroxymethyl-2,1,3-benzothiadiazole 1,[56] was reduced with Raney nickel to yield 2,3-diaminobenzyl alcohol 2. Using the copper acetate coupling conditions,[55] the phenyl-benzimidazole backbone was formed from reaction of the 2,3-diaminobenzyl alcohol 2 with 2-nitrophenyl-1-carboxaldehyde in 82% yield. The benzyl alcohol group of 3 was oxidized to the corresponding aldehyde by manganese dioxide and then protected as the acetal 5. With both the aldehyde protected as the acetal and the amine protected as the nitro group, substitution at the benzimidazole nitrogen position can be achieved fairly easily. For example, a methyl group can be added by treatment of 5 with methyl iodide in the presence of sodium hydride. Other substituents have also been added via similar procedures, providing for a wide range of bis-benzimidazole derivatives. Reduction of the nitro group of 6 with hydrogen, catalyzed by Pd on carbon, followed by the addition of perchloric acid, unmasked both the amine and carboxaldehyde functionalities. Dimerization and cyclization of the resulting precursor gave the desired Me$_2$BBZ ligand.

Various metal complexes of the ligand are prepared by neutralization of the diprotonated ligand followed by addition of the appropriate metal salt.

Materials and Methods $^1$H NMR spectra were recorded on a Bruker WM 200 (200 MHz) spectrometer. Spectra were referenced internally to the residual proton resonance of CDCl$_3$ (d 7.26 ppm) as the internal standard. Chemical shifts (δ) were reported as part per million (ppm) in δ scale. Coupling constant (J) are reported in Hertz (Hz). NMR spectroscopic terms are reported by using the following abbreviations: s, single; d, double; t, triplet; m, multiplet.

Unless otherwise noted, all materials were obtained from commercial suppliers and used without further purification. Thin layer chromatography was performed on Whatman precoated silica gel VV$_{254}$ plates. Silica gel (32–63 m) was used for column chromatography.

2,3-Diaminobenzyl alcohol (2)

Raney nickel (~5 g) was placed in a hydrogenation bottle and washed with THF three times before being slurried in 50 mL of THF. 4-Hydroxymethyl-2,1,3-benzothiadiazole[56] (5.0 g, 30 mmol) was then added. It was hydrogenated under 10 psi pressure at room temperature for 6 hours. TLC was used to confirm that all starting material had been consumed. The reaction mixture was then filtered carefully through a pad of celite and washed with THF. After removal of the solvent, 2,3-diaminobenzyl alcohol (4.0 g, 96%) was obtained as a colorless crystalline solid. R$_f$=0.18 (hexane/ethyl acetate/ MeOH=5:5:1); $^1$H NMR (200 MHz, DMSO) δ 4.33 (broad s, 2H), 4.36 (d, J=5.4 Hz, 2H), 4.43 (broad s, 2H), 4.96 (t, J=5.4 Hz, 1H), 6.43 (m, 3H); HRMS: Calcd. for C$_7$H$_{10}$N$_2$O 138.0793, found 138.0830.

4-Hydroxymethyl-2-(2-nitrophenyl)-benzimidazole (3)

2,3-Diaminobenzyl alcohol 2 (3.45 g, 25 mmol) was dissolved in a MeOH/H$_2$O mixture (200 mL, v/v=1:1). Acetic acid (3 mL), 2-nitro-benzaldehyde (5.3 g, 35 mmol) in MeOH (50 mL) and Cu(OAc)$_2$·H$_2$O (7.0 g, 35 mmol) in water (100 mL), were added sequentially to the stirring solution. It was then heated to reflux under vigorous stirring for 3 hr, after which a pale yellow precipitate was formed. The mixture was filtered hot and then washed with water to afford a gray-yellow solid. The precipitate was redissolved in EtOH (150 mL) and concentrated HCl (24 mL), and then a solution of Na$_2$S·9H$_2$O (12.8 g, 50 mmol) in water (100 mL) was added. The mixture was heated at reflux for 1 hour resulting in a black slurry. It was then allowed to cool to room temperature, and filtered through a pad of celite to remove the resulting CuS. The filtrate was neutralized with ammonium hydroxide to pH=8–9 and then concentrated by rotary evaporation to yield a green-yellow precipitate. After filtration and vacuum evaporation, 4-hydroxymethyl-2-(2-nitrophenyl)-benzimidazole (5.55 g, 82%) was obtained as a green-yellow solid. R$_f$=0.28 (hexane/ethyl acetate=1:2); $^1$H NMR (200 MHz, DMSO) δ 4.84 (broad s, 2H), 5.22 (broad s, 1H), 7.28 (m, 2H), 7.49 (d, J=6.8 Hz, 1 H), 7.71–8.06 (m, 4H), 12.93 (broad s, 1H); HRMS: Calcd. for C$_{14}$H$_{11}$N$_3$O$_3$ 269.0800, found 269.0845.

2-(2-Nitrophenyl)-benzimidazole-4-carboxaldehyde (4)

4-Hydroxymethyl-2-(2-nitrophenyl)-benzimidazole 3 (2.69 g, 10 mmol) was dissolved in a mixture of CH$_3$CN/ CH$_2$Cl$_2$ (500 mL, v/v=4:1), and then manganese dioxide (10 g, 120 mmol) was added. The solution was stirred at room temperature and monitored by TLC. Once the reaction was complete, the reaction mixture was filtered through a pad of celite. The filtrate was washed with NaHCO$_3$, and the water phase was extracted with CH$_2$Cl$_2$. The combined organic layer was washed with brine and dried over Na$_2$SO$_4$. Concentration by rotary evaporation and subsequent column chromatography on silica gel using hexane/ethyl acetate (1:1) as the eluent afforded 2-(2-nitrophenyl)-benzimidazole-4-carboxaldehyde (2.2 g, 82%) as a light-yellow solid. R$_f$=0.38 (hexane/ethyl acetate=1:1); $^1$H NMR (200 MHz, CDCl$_3$) δ 7.47 (t, J=7.6 Hz, 1H), 7.63–7.82 (m, 3H), 7.94 (d, J,=7.5 Hz, J$_2$=1.5 Hz, 1H), 8.05 (d, J$_1$=7.7 Hz, J$_2$=1.6 Hz, 1H), 8.10 (d, J=8.1 Hz, 1H), 10.11 (s, 1H), 11.21 (broad s, 1H); HRMS: Calcd. for C$_{14}$H$_9$N$_3$O$_3$ 267.0644, found 267.0648.

2-(2-Nitrophenyl)-benzimidazole-4-carboxaldehyde ethylene acetal (5)

2-(2-Nitrophenyl)-benzimidazole-4-carboxaldehyde 4 (6.27 g, 23.5 mmol) was dissolved in benzene (150 mL), and mixed with ethylene glycol (6.5 mL, 118 mmol) and p-toluenesulfonic acid monohydrate (0.450 g, 2.35 mmol). The mixture was heated to reflux overnight and the water was removed by azeotropic distillation. The resulting solution was allowed to cool to room temperature, and was then neutralized with saturated NaHCO$_3$, washed with water and brine and dried over Na$_2$SO$_4$. The compound was purified by column chromatography on silica gel using hexane/ethyl acetate (1:2) as the eluent to give 2-(2-nitrophenyl)-benzimidazole-4-carboxaldehyde ethylene acetal (4.552 g, 62.2%) as a yellow solid. R$_f$=0.24 (hexane/ethyl acetate= 1:2); $^1$H NMR (200 MHz, CDCl$_3$) δ 4.11 (m, 2H), 4.20 (m, 2H), 6.15 (s, 1H), 7.30 (m, 2H), 7.57–7.83 (m, 3H), 7.93 (d, J$_1$=7.8 Hz, J$_2$=1.3 Hz, 1H), 8.13 (d, J$_1$=7.7 Hz, J$_2$=1.5 Hz, 1H), 10.48 (broad s, 1H). HRMS: Calcd. for C$_{16}$H$_{13}$N$_3$O$_4$ 311.0906, found 311.0915.

1-Methyl-2-(2-nitrophenyl)-benzimidazole-4-carboxaldehyde ethylene acetal (6)

A solution of 2-(2-nitrophenyl)-benzimidazole-4-carboxaldehyde ethylene acetal 5 (4.53 g, 14.6 mmol) in dry THF (20 mL) was added to a stirring suspension of NaH (0.640 g, 60% dispersion in mineral oil, 16.0 mmol) in dry THF (50 mL) at 0° C. under N$_2$. The mixture was then allowed to warm to room temperature for 1 hour resulting in an orange solution. Methyl iodide (4.58 mL, 72.8 mmol) was syringed into the above mixture at room temperature under N$_2$. This mixture was stirred for 24 hours under N$_2$ to give a yellow mixture. Water was added and the aqueous layer was extracted with CHCl$_3$. The combined extracts were washed with brine and dried over Na$_2$SO$_4$. After rotary evaporation, the resulting residue was purified by column chromatography on silica gel using Et$_2$O:CH$_2$Cl$_2$ (3:1) as the eluent to give the title compound. (3.53 g, 74%). $^1$H NMR (CDCl$_3$): δ 3.58 (s, 3H), 4.02–4.19 (m, 4H), 6.55 (s, 1H), 7.33–7.41 (m, 1H), 7.52–7.56 (m, 1H), 7.62–7.75 (m, 4H), 8.19 (d, J=1.7, 7.9 Hz, 1H); HRMS: Calcd. for C$_{17}$H$_{15}$N$_3$O$_4$ 325.1062, found 325.1050.

1-Methyl-2-(2-aminophenyl)-benzimidazole-4-carboxaldehyde ethylene acetal (7)

A solution of 6 (0.85 g, 2.6 mmol) in 50 mL MeOH was mixed with 85 mg of Pd/C and hydrogenated with H$_2$ at a pressure of 10 psi for 3 hours. The mixture was then filtered, and the solvent was removed to give 0.76 g (98%) of the title compound as a white solid. $^1$H NMR (CDCl$_3$): δ 4.44 (s, 3H), 4.69–4.90 (m, 4H), 5.69 (broad s, 2H), 7.44 (d, J=7.8 Hz, 2H), 7.81–8.05 (m, 4H), 8.14 (d, J=1.6, 6.9 Hz, 1H); HRMS: Calcd. for C$_{17}$H$_{17}$N$_3$O$_2$ 295.1321, found 295.1325.

[H$_2$(Me$_2$BBZ)](ClO$_4$)$_2$ (8)

1-Methyl-2-(2-aminophenyl)-benzimidazole-4-carboxaldehyde ethylene acetal (7) (0.62 g, 2.1 mmol) was dissolved in CH$_3$CN (15 mL) at room temperature, and then perchloric acid (0.42 mL, 2.3 mmol) was added. The mixture was stirred at room temperature for 2 days to yield a white suspension. It was then filtered to give the title compound as a white powder (0.56 g, 80%). $^1$H NMR (DMSO): δ 4.06 (s, 6H), 7.63–7.73 (m, 6H), 7.81 (t, J=8.0 Hz, 2H), 7.94 (t, J=7.6 Hz, 2H),), 8.04 (d, J=7.4 Hz, 2H), 8.10 (d, J=7.2 Hz, 2H), 8.26(d, J=8.2 Hz, 2H), 8.94 (s, 2H). Crystals suitable for X-ray analysis were obtained from recrystallization from CH$_3$CN.

Structure of [H$_2$(Me$_2$BBZ)](ClO$_4$)$_2$

The crystal used for data collection was a yellow plate. Examination of the diffraction pattern on a Siemens SMART diffractometer with a CCD area detector (Siemens CCD 1K) at the University of Toledo's Instrumentation Center indicated a monoclinic system. Unit cell constants were obtained by a least-squares fit for 6397 reflections using graphite monochromated MoKα radiation (λ=0.71073 Å). A full sphere of data was measured and data integration was done with the SAINT software (version 5.0, Bruker Analytic X-ray Systems). The data was 88% complete out to 2θ=55°. A correction for absorption of the incident and diffracted beams was applied to the data with the SADABS program,[75] with the maximum and minimum effective transmission factors of 1.0 and 0.797. Averaging the symmetry equivalent reflections results in an R$_{int}$ value of 0.056.

The structure was solved by direct methods in SHELXS-86.[76] Full-matrix least-squares refinements based on F$^2$ were performed in SHELXL-93.[77] While both perchlorate groups had large displacement parameters for the oxygen atoms, one group was better behaved that the other. An attempt was made to model the disorder in the perchlorate containing Cl(2). There appears to be a second orientation for this group which can be obtained by rotating about the Cl(2)-O(5) bond. The occupancy factors for O(6), O(7) and O(8) were each set at 0.65, while those for O(6A), O(7A), and were set at 0.35. Cl(2) and O(5) were refined anisotropically, while the disordered oxygen atoms were refined isotropically. O(8A) acquired a very large U value, while all the other oxygen atoms refined to fairly reasonable U values. As a result, O(8A) was removed from the model.

The hydrogen atoms were included in the model at calculated positions using a riding model with U(H)= 1.2*U$_{eq}$(attached carbon atom). For a methyl group, the torsion angle which defines its orientation was allowed to refine, and these hydrogen atoms were assigned U(H)= 1.5*U$_{eq}$(attached carbon atom). The final refinement cycle was based on all the 6703 intensities and 410 variables and resulted in agreement factors of R$_1$(F)=0.169 and wR$_2$(F$^2$)= 0.258. For the subset of data with I>2σ(I) the R$_1$(F) value is 0.097 (for 3768 reflections). The large R-factors are a result of the difficulty in modeling the disordered perchlorate group and the fact that the data set was rather weak. The final difference electron density map contains maximum and minimum peak heights of 1.01 and –0.92 e/Å$^3$. The maximum peak is in the vicinity of the disordered perchlorate ion. Neutral atom scattering factors were used and include terms for anomalous dispersion.[78]

X-ray Structure

Figure 3:
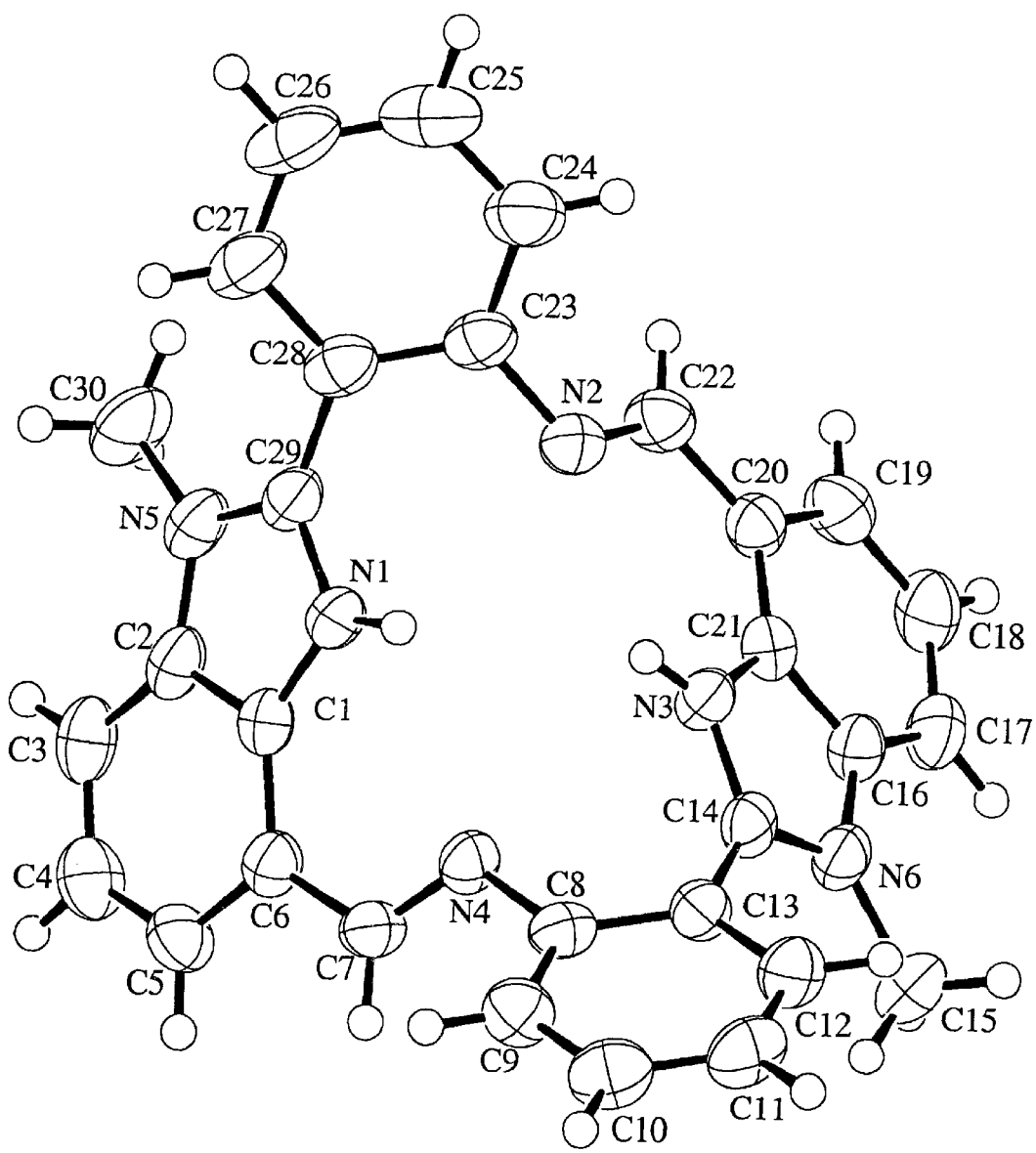
FIG. 3. is an ORTEP diagram of [H$_2$(Me$_2$BBZ)](ClO$_4$)$_2$.

The correct identity of the Me$_2$BBZ ligand was confirmed by the crystal structure of its diprotonated form shown in FIG. 3 (see Tables 1 and 2). The structure clearly shows that the benzimidazole framework is methylated on the outer benzimidazole nitrogens, N(5) and N(6), and that protonation occurs on the inner benzimidazole nitrogens, N(1) and N(3). The structure of the free ligand exhibits significant distortion from planarity. This is significant because it demonstrates that the observed ruffling of Me$_2$BBZ is intrinsic to the ligand, and is independent of bound metal.

Synthesis of [Mn(Me$_2$BBZ)Cl]Cl (9)

Perchloric acid (0.185 mL, 2.15 mmol) was added to a solution of 7 above (0.634 g, 2.15 mmol) in CH$_3$CN. The resulting pale yellow solution was stirred for 20 hours. Et$_3$N (0.5 mL, 13.6 mmol) was then added to form a yellow suspension that was stirred for 2 hours, at which point, the solvent was removed by rotary evaporation. The product was triturated with water, filtered and washed with CH$_3$CN, and then dried at room temperature to give the free Me$_2$BBZ ligand as a pale yellow solid (0.45 g, 90%). HRMS: Calcd. for C$_{30}$H$_{22}$N$_6$ 466.1906, found 466.1914.

The [Mn(Me$_2$BBZ)Cl]Cl complex 9, was prepared by refluxing the unpurified free Me$_2$BBZ ligand with MnCl$_2$.4H$_2$O in CH$_3$CN. Purification by column chromatography gave an orange solid in 82.0% yield. (Calcd. for [Mn(Me$_2$BBZ)Cl]Cl.4H$_2$O: C, 54.23; H, 4.55, N 12.65; Found: C; 54.83, H, 4.17, N, 12.73). Crystals of the [Mn(Me$_2$BBZ)Cl]Cl complex suitable for X-ray analysis were obtain by evaporation from MeOH/EtOH.

In another run, the [Mn(Me$_2$BBZ)Cl]Cl complex (9) was prepared by refluxing the unpurified free Me$_2$BBZ ligand (0.497 g, 0.92 mmol) with MnCl$_2$.4H$_2$O (0.1824 g, 0.92 mmol) in CH$_3$CN. An orange mixture was obtained upon stirring. The solution was refluxed for 20 hours and then the solvent was removed by rotary evaporation. The crude product was purified by column chromatography (CH$_2$Cl$_2$:Hexane:MeOH=3:1:1) (R$_f$=0.73) and then dried to give an orange solid (0.45 g, 82% yield). Crystals of the [Mn(Me$_2$BBZ)Cl]Cl complex suitable for X-ray analysis were obtain by evaporation from CH$_3$CN. (Calcd. for [Mn(Me$_2$BBZ)Cl]Cl.4H$_2$O: C, 59.03; H 3.93, N, 13.77; Cl 11.62; Found: C, 57.97; H, 3.84; N, 13.39; Cl, 12.27).

Structure of [Mn(Me$_2$BBZ)Cl]Cl

The crystal used for data collection was an orange-red irregular plate. Examination of the diffraction pattern on a Siemens SMART diffractometer with a CCD area detector (Siemens CCD 1K) at the University of Toledo's Instrumentation Center indicated a triclinic crystal system. Unit cell constants were obtained by a least-squares fit for 3807 reflections using graphite monochromated MoKα radiation (λ=0.71073 0). A full sphere of data was measured using the ω scan method with narrow frames of 0.30°. Data integration was done with the SAINT software (version 5.0, Bruker Analytic X-ray Systems). The data is 89.2% complete out to 2θ=60 and 98.6% complete out to 2θ=55°. A correction for absorption of the incident and diffracted beams was applied to the data with the SADABS program,[75] with the maximum and minimum effective transmission factors of 1.0 and 0.822. Averaging the symmetry equivalent reflections results in an R$_{int}$ value of 0.049.

The structure was solved by the Patterson method using SHELXS-86[76] in P1 bar. Full-matrix least-squares refinements based on F$^2$ were performed in SHELXL-93.[77] The Mn complex packs in such a manner that channels are formed which run along the a axis direction and are centered at y=z=0. The Cl$^-$ ion resides in this channel along with some disordered water molecules. As it was difficult to obtain a satisfactory model of the water molecules in this channel, the density in this channel was accounted for by the SQUEEZE program[79] of PLATON.[80] This program modifies the observed structure factors by subtracting away contributions to them based on the electron density in the channel. In this case, the contributions of all of the electron density in the channel, including the Cl$^-$ ion, were subtracted from the observed structure factors. (This is the reason why no positional coordinates for the Cl$^-$ ion appear in the table of atomic coordinates in the Supplementary Material). This channel region occupies 244 Å$^3$ per unit cell and the electron density removed by this SQUEEZE procedure amounts to 41 electrons/unit cell. This corresponds to two Cl$^-$ anions and one water molecule per unit cell.

The hydrogen atoms were included in the model at calculated positions using a riding model with U(H)= 1.2*U$_{eq}$(attached carbon atom). For a methyl group, the torsion angle which defines its orientation was allowed to refine, and these hydrogen atoms were assigned U(H)= 1.5*U$_{eq}$(attached carbon atom). The (0 2 2) reflection was omitted from the final refinements as it had a significantly larger delta(F$^2$)/esd value than the other reflections. The final refinement cycle was based on all the 7289 intensities and 345 variables and resulted in agreement factors of R$_1$(F)= 0.128 and wR$_2$(F$^2$)=0.120. For the subset of data with I>2σ(I) the R$_1$(F) value is 0.051 (for 3638 reflections). The final difference electron density map contains maximum and minimum peak heights of 0.23 and −0.23 e/Å$^3$. Neutral atom scattering factors were used and include terms for anomalous dispersion.[78]

X-ray Structure

Figure 4:
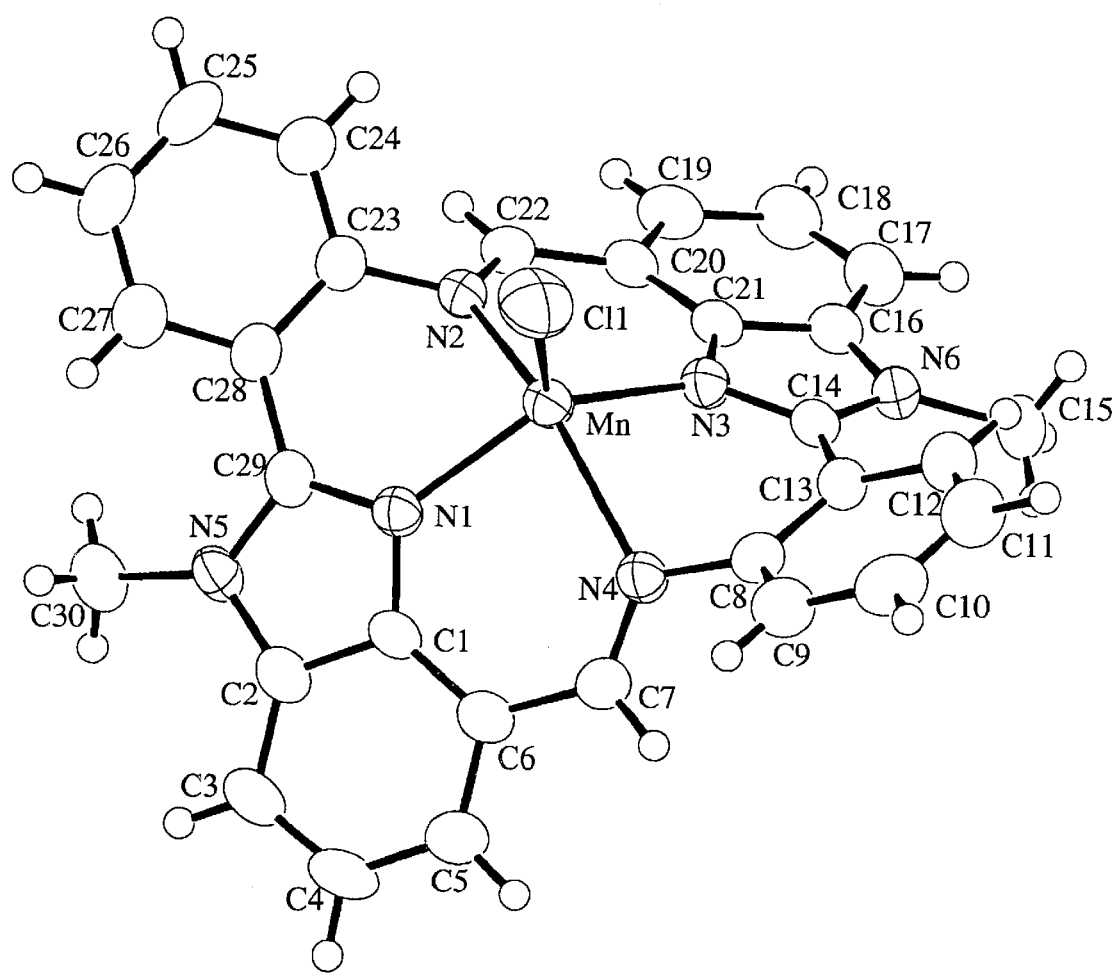
FIG. 4. is an ORTEP diagram of [Mn(Me$_2$BBZ)Cl]Cl.

The structure of the [Mn(Me$_2$BBZ)Cl]Cl complex is shown in FIG. 4 (see Tables 1 and 3). For consistency, the atom labeling scheme used for the free Me$_2$BBZ ligand is used for the manganese complex as well. The complex was crystallized as the dichloride salt. Like most Mn(II) porphyrins, the manganese ion in the [Mn(Me$_2$BBZ)Cl]Cl complex is five coordinate and the metal exhibits a distorted square pyramidal geometry with average bond distances of 2.12 Å for the Mn—N(benzimidazole) and 2.26 Å for the Mn—N(imine) nitrogens. One of the chlorides binds the manganese ion with a Mn—Cl distance of 2.319 Å.

In a general sense, the structure does show some bonding similarities to classical tetrapyrrole complexes (porphyrins and phthalocyanines) as the ligand coordinates the manganese ion in the equatorial plane. Moreover, the Mn—N (benzimidazole) and Mn—Cl distances of the Mn(II) (Me$_2$BBZ)Cl$_2$ complex are similar to structurally characterized five-coordinate Mn(II) porphyrins which have average Mn—N(porphyrin) bond distances of 2.1 Å and Mn—Cl(axial) distances of 2.37 Å.[57,58] The Mn(II)-N (imine) distances of the [Mn(Me$_2$BBZ)Cl]Cl complex are longer, however. Similar comparisons to phthalocyanines, are complicated by the fact that no five coordinate Mn(II) phthalocyanines have been structurally characterized. Four coordinate Mn(II) phthalocyanines, however, have been isolated, and show shorter Mn(II)-N(pyrrole) bond distances of 1.94 Å.[59,60] The smaller "central hole" size in phthalocyanines compared to porphyrins has been used to explain this difference. These explanations could be relevant to the Me$_2$BBZ ligand as well.[59]

Non-planar distortions are typically observed for metal tetrapyrrole complexes. Similarly, both the free Me$_2$BBZ ligand and [Mn(Me$_2$BBZ)Cl]Cl complex exhibit non-planar distortions, although the type of distortion is distinct and the magnitude of the distortion is significantly larger. The typical distortions characterized for porphyrins are the ruf (ruffle), sad (saddle), the dom (dome), and the wav (wave) distortions. The ruf distortion is the most common and has biological relevance. This distortion has been observed for all mitochondrial c-type cytochromes isolated from different species.[32,33] The sad distortion is the next most common. It is characterized by having each pairs of $C_b$ carbons on each pyrrole alternately displaced above and below the mean porphyrin plane.[61] This mode of distortion is unique to tetraphenylporphyrin complexes and their derivatives.[61,62] Interestingly, five-coordinate Mn(II) porphyrins differ from these more common $D_{2d}$ distortions and adopt the dom geometry in which the metal is displaced slightly upwards from the ligand plane.

The distortions exhibited by the [Mn(Me$_2$BBZ)Cl]Cl complex and all other metallated forms (Co, Fe, Ni, Zn) were distinct from any of the four classical modes observed for porphyrins or other tetrapyrroles. Instead, they adopt a conformation that appears to be a mixture of the ruf and sad distortions. Like the ruf distortion, the opposite pyrrole and schiff base groups are counter-rotated. Like the sad distortion, the alternate liganding groups are displaced above and below the ligand plane. We refer to this new type of distortion as a twist. It is apparent that the geometric constraints in bis-benzimidazoles limits the possible degrees of freedom and force the two groups of atoms within each phenylbenzimidazole subunit to lie on a line (atoms C(29), C(28), and C(25) being one set, and atoms C(10), C(13), and C(14) being the other). This limits the possible degrees of freedom. The net effect is a significantly twisted ligand with two distinct and well-defined ligand planes. Interestingly, while -conjugation would favor a planar geometry for each of the phenylbenzimidazole groups, the driving force for distortion of the overall macrocycle is sufficient to cause each of the phenylbenzimidazole units to twist as well.

In light of the differences in the type of distortion and the nature of the ligand, a direct comparisons of the magnitudes of the distortions observed between bis-benzimidazoles, and porphyrins (and phthalocyanines) is not entirely straightforward. One way is to compare the distance of central metal ion from the mean ligand plane. For instance, in both Mn(II) porphyrins and the [Mn(II)(Me$_2$BBZ)Cl]Cl complex, the central Mn ion is significantly shifted away from the mean ligand plane. In the case of Mn(II) porphyrins, the distance of the Mn ion from the mean porphyrinato plane has been reported as 0.56 Å for Mn(II)(TPP)(1-methylimidazole)[57,63] and 0.614 Å for Mn(II)(TPP)Cl.[58] In the present study, the Mn ion of the [Mn(II)(Me$_2$BBZ)Cl]Cl complex is shifted 0.796 Å from the mean plane of the four nitrogen ligands, and 1.05 Å from the mean plane formed from the 22 atoms which are conserved between porphyrins and the Me$_2$BBZ ligand. These data reveal significantly larger metal distortions for metal Me$_2$BBZ complexes than metalloporphyrins.

In porphyrins, the displacement of the $C_m$ and $C_b$ carbons are commonly used to estimate the extent of the distortion.[62] In the case of the bis-benzimidazole complex here, the $C_m$ atoms correspond to C(6), C(13), C(20), and C(28), while the $C_b$ atoms correspond to N(5), C(2), C(9), N(6), C(16), and C(24). Values of the maximum $C_m$ and $C_b$ displacements for several Mn(II) porphyrins and the values for the corresponding atoms in the two Me$_2$BBZ structures reported in this work, are tabulated in Table 4. These data indicate that the ligand distortions observed for the two Me$_2$BBZ compounds are significantly larger than those typically exhibited by typical porphyrins.

Figure 5:
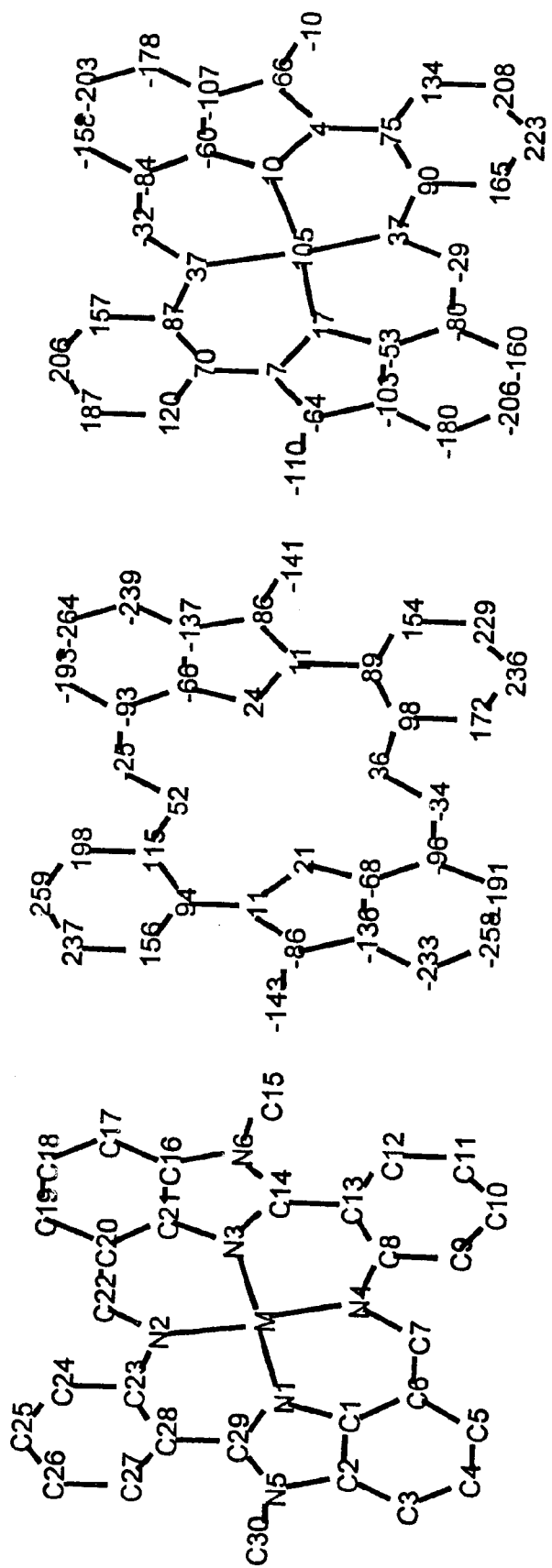
FIG. 5. contains diagrams of the bis-benzimidazole cores. Labeling scheme, (left); [H$_2$(Me$_2$BBZ)](ClO$_4$)$_2$ (8), (center); [Mn(Me$_2$BBZ)Cl]Cl (9), (right). The perpendicular displacement of each atom, in units of 0.01 Å, from the mean place of the 22 atoms in common with porphyrins is given.

Comparisons of different bis-benzimidazoles is much easier, since all the ligand atoms are the same. Using the mean ligand plane formed from the atoms which are conserved between porphyrins and bis-benzimidazoles, the distance of each atom from this plane was calculated for both the diprotonated Me$_2$BBZ ligand and [Mn(Me$_2$BBZ)Cl]Cl complex. These distances are shown in FIG. 5. The larger absolute shifts (both above and below the plane) for the atoms in the diprotonated Me$_2$BBZ ligand indicate that the diprotonated Me$_2$BBZ ligand is more distorted. These data also reveal that the twist distortion is inherent to the Me$_2$BBZ ligand and is not a consequence of metal binding, as it is in the case for many porphyrins.

Analysis of the structures of the diprotonated Me$_2$BBZ ligand and [Mn(Me$_2$BBZ)Cl]Cl complex suggest that the driving force for the twist distortion stems from two types of steric interactions: (1) interactions between the protons of C(7) and C(9), and the protons of C(22) and C(24); and (2) interactions within each phenylbenzimidazole group between the methyl substituent and the neighboring phenyl ring (the C(15) methyl group with C(11)-H, and the C(30) methyl group with C(27)-H (FIGS. 3 and 4). The latter set of interactions are particularly important, because they suggest that incorporation of larger substituents could lead to even larger distortions.

Crystal Packing in Mn—Me$_2$BBZ

Perhaps the most exciting feature of the bis-benzimidazole ligand is its potential for asymmetric catalysis. Because of the lower C2 symmetry of the bis-benzimidazole macrocycle compared to the porphyrin and the phthalocyanine, there exist two distinct atrophisomers with high barriers to interconversion, particularly in the case of its metal complex. In light of the extreme distortions from planarity observed, it is believed that each of the separated isomers of the bis-benzimidazoles ligand could be used to mediate chiral catalysis at a metal center.

Figure 6:
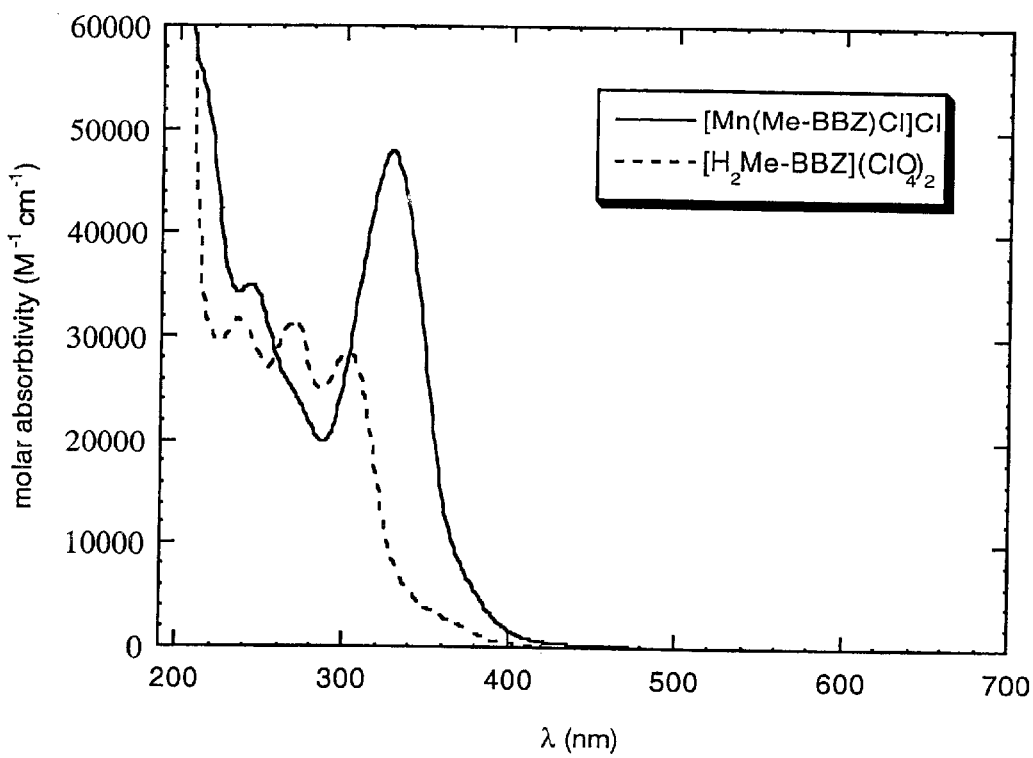
FIG. 6 is a stereo view of the two-dimensional "staircase" layer. The L·7·L·7 benzimidazole stacking interactions are aligned horizontally. The phenyl-phenyl stacking interactions are aligned vertically. The channel lies at the origin. (bottom) Perpendicular view showing arrays of aligned atropisomers. Binding of ligands between successive molecules could potentially lead to donor-acceptor chains.

That is to say, analysis of the crystal packing interactions in the Mn—Me$_2$BBZ crystals reveals another interesting consequence of the unusual Me$_2$BBZ ligand geometry. Due to the twist of the Me$_2$BBZ ligand and the fixed planarity of the phenyl and benzimidazole units, [Mn(Me$_2$BBZ)Cl]$^+$ molecules arrange themselves into two dimensional layers comprised of alternating [Mn(Me$_2$BBZ)Cl]$^+$ atropisomers (FIG. 6). In the crystal, each Mn—Me$_2$BBZ complex interacts with three other molecules of the opposite hand via π-stacking interactions (FIG. 6). Two of the intermolecular π-stacking interactions involve benzimidazole rings of adjacent [Mn(Me$_2$BBZ)Cl]$^+$ molecules. These interactions are found on opposing sides of the Mn—Me$_2$BBZ complex, such that if "L" represents one hand and "7" the other, then linear L·7·L7·L·7 chains are formed along the direction of the benzimidazole stacking. The distance between stacked benzimidazole rings is 3.44 and 3.35 Å for the two distinct L·7 and 7·L stacking interactions, respectively. The third intermolecular interaction involves the phenyl rings of two [Mn(Me$_2$BBZ)Cl]$^+$ molecules located on different L·7·L7·L·7 chains. The intermolecular distance between the phenyl rings here is 3.85 Å. Only one of the two phenyl rings of each [Mn(Me$_2$BBZ)Cl]$^+$ molecule is involved in intermolecular interactions. The other phenyl ring forms one side of an intermolecular channel.

Because the phenyl and benzimidazole stacking interactions within the Mn—Me$_2$BBZ crystal are directed in perpendicular directions, they generate an unusual lattice comprise of two-dimensional "staircase" layers. These layers lie in the plane generate by the a and b axes in the crystal, termed the C-plane. The three-dimensional lattice is generated by translation of these "staircase" layers by one unit cell length along the c-axis resulting in stacks of "staircase" layers, each of which is slightly horizontally shifted from the layer above and below.

Because of the low symmetry of the crystal, molecules of the same hand lie above one another along the c-axis. This results in the formation columnar chains of [Mn(Me$_2$BBZ)Cl]$^+$ units directed in the +c and −c directions. The axial ligand in each chain is directed along the c-axis as well. Importantly, as in porphyrins, covalent interactions between bisbenzimidazole units must occur through their axial ligands. Hence, this arrangement offers the possibility of generating covalent donor-acceptor chains along the c-axis.

Perhaps of greater significance is the fact that the extensive π-stacking interactions within the Mn—Me$_2$BBZ crystal promote greater cohesion of the molecular bisbenzimidazole units than are typically found in crystals of metalloporphyrins or phthalocyanines. Within each layer, the intermolecular Mn-Mn distances are 8.997 Å and 8.971 Å through the two 7·L and L·7 benzimidazole-stacking interactions, respectively, and 11.400 Å through the phenyl-stacking interaction. The distance between layers is the length of the c-axis or 14.373 Å.

These intermolecular interactions could be of particular importance in the design and synthesis of materials that require cooperative electronic and/or magnetic couplings. For example, in the molecular magnet formed from linear chains of [MnTPP]$^+$[TCNE]$^-$ donor-acceptor pairs, ferro- or ferrimagnetic interchain coupling is a requirement for observed ferrimagnetic behavior. In crystals of [MnTPP]$^+$[TCNE]$^-$, the intermolecular Mn—Mn separations across the chains are 13.269 and 14.932 Å for atoms in the same plane, while the out-of registry Mn—Mn separations are 11.006, 11.823, and 13.838. As the strength of the electronic and magnetic coupling is distance dependent, the shorter Mn—Mn interchain distances in Mn—Me$_2$BBZ crystals compared to corresponding porphyrin and phthalocyanine crystals, suggests that the Mn—Me$_2$BBZ "staircase" layer could be a favorable structural motif for the design of novel materials. Studies designed to take advantage of these observations are currently underway.

Optical Properties

Figure 7:
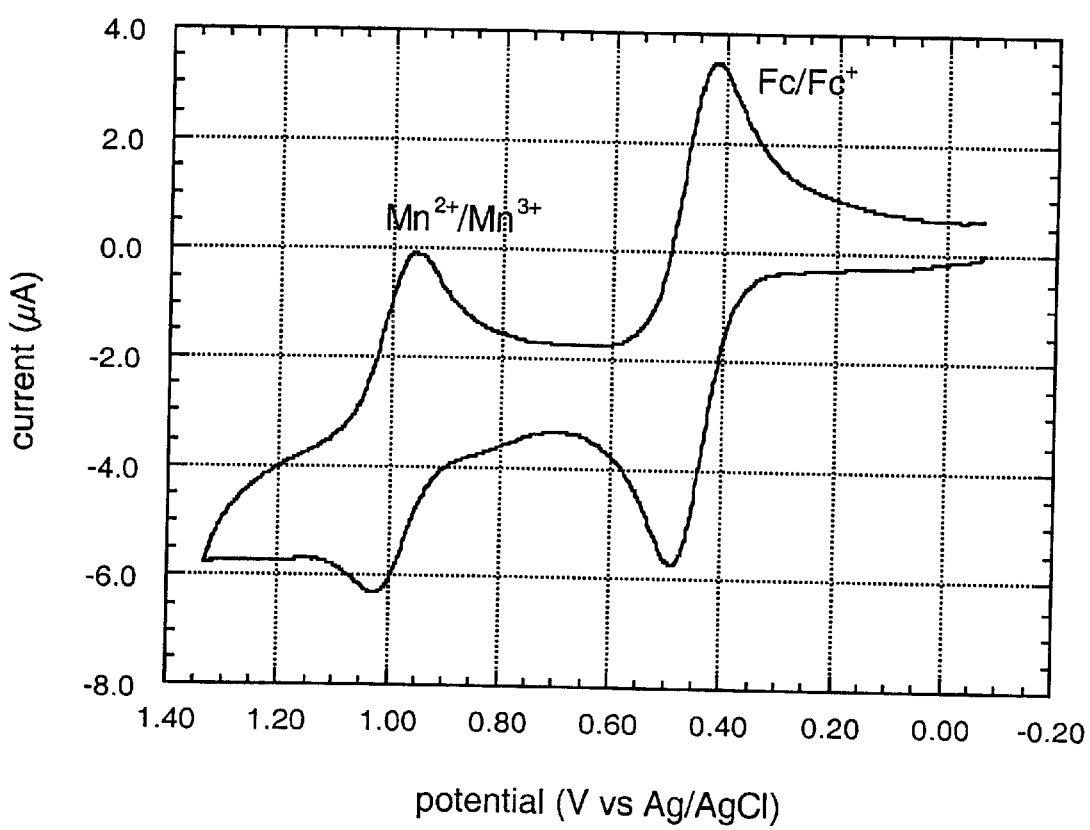
FIG. 7. shows the optical spectrum of the diprotonated [H$_2$(Me$_2$BBZ)](ClO$_4$)$_2$ ligand and the [Mn(Me$_2$BBZ)Cl]Cl complex.

Porphyrins typically show a strong Soret band near 400 nm and lower energy Q-bands around 600 nm arising from π–π* transitions.[64–66] Phthalocyanines behave similarly: a strong ultra-violet Soret absorption occurs in the 320–370 nm region and Q band absorptions are observed in the vicinity of 670–690 nm.[67,68] The optical spectrum of the diprotonated Me$_2$BBZ ligand is shown in FIG. 7. Major bands are observed at 235 nm (ϵ=3.17×10$^4$), 270 nm (ϵ=3.14×10$^4$), and 302 nm (ϵ=2.84×10$^4$) for the diprotonated ligand. In the [Mn(Me$_2$BBZ)Cl]Cl complex, the high energy absorption shifts somewhat to 243 nm (ϵ=3.50×10$^4$) and 328 nm (ϵ=4.78×10$^4$). As expected, the π–π* transitions in the cyclic bis-benzimidazoles occur at higher energies. Unlike porphyrins and phthalocyanines, however, there is no evidence of a low energy Q band absorption in bis-benzimidazoles.

The similarity of these optical energies and extinction coefficients among bis benzimidazoles and classical tetrapyrroles suggest that the spectra of the Me$_2$BBZ ligand and Mn—Me$_2$BBZ complex likely result from π–π* transitions as well. Unlike porphyrins and phthalocyanines, however, bis benzimidazoles do not appear to exhibit the low energy Q band absorption. One interesting consequence of the absence of Q band is a lack of significant absorptions in the visible spectrum (from 500–900 nm). This outcome could have important ramifications for the practical use of bis benzimidazoles in non-optical materials—particularly those applications where visible absorptions would be detrimental.

Electrochemical Properties

Figure 8:
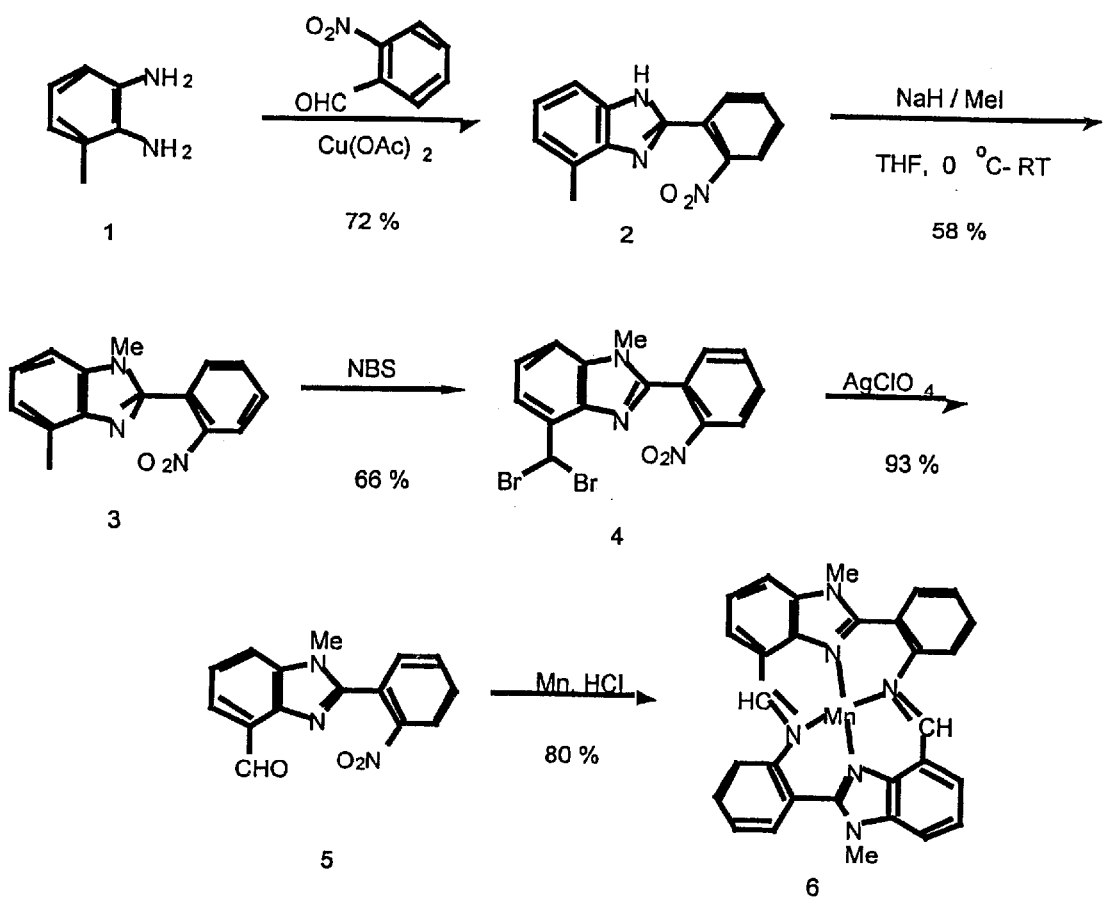
FIG. 8. is a cyclic voltamogram of [Mn(II)(Me$_2$BBZ)Cl] Cl.4H$_2$O in acetonitrile/0.10 M Bu$_4$NClO$_4$ with ferrocene as internal reference. Scan rate=100 mV/sec, 1.0 mm Pt disk working electrode, Pt wire counter electrode, Ag/Ag$^+$ quasi-reference electrode.

The protonated Me$_2$BBZ ligand shows no reversible electrochemistry. In contrast, the [Mn(II)(Me$_2$BBZ)Cl]Cl complex displays a reversible ($\Delta E_{peak}$=66 mV) Mn(II)/Mn(III) oxidative couple in acetonitrile with an $E_{1/2}$ around 1.0 volts versus Ag/AgCl (FIG. 8). While similar oxidation potentials are observed for manganese porphyrins (~1.0 V vs. SCE), the redox couple is between the Mn(III)/Mn(IV) oxidation states, while the corresponding manganese porphyrin Mn(II)/Mn(III) redox potentials are generally around −0.2 V.[69,70] Mn(II) phthalocyanines exhibit similar potentials to porphyrins with Mn(II)/Mn(III) redox couples at −0.1 V versus SCE, and a second oxidative potential at 0.86 V versus SCE. However, the latter redox couple is speculated to originate from the oxidation of the phthalocyanine ligand itself, and not further oxidation of the metal center.[71]

These data suggest that porphyrins and phthalocyanines are better at stabilizing higher oxidation state species than bis-benzimidazoles. This is not surprising in light of the difference in the charge between the two types of ligands. While deprotonation of the free ligand of porphyrins and phthalocyanines, as required to bind a metal ion, results in a dianionic tetrapyrrole, in the case of bis-benzimidazoles, deprotonation of the diprotonated ligand results in a neutral species. The negatively charge porphyrin and phthalocyanine would be more likely to provide electron donation to the metal, and hence, should be in a better position to stabilize the higher oxidation states. In this connection, we note that the unsubstituted bis-benzimidazole ligand would also be dianionic, and therefore, could have redox properties more similar to porphyrins. The unsubstituted ligand should also exhibit greater aromaticity, as in porphyrins.

X-band EPR Spectra of the Mn—Me$_2$BBZ Complex

A 5 mg/mL sample of the Mn—Me$_2$BBZ complex was dissolved in methanol/ethanol solution and frozen under liquid nitrogen to obtain a suitable glass. The EPR experiments were performed with a Varian E-109 X-band spectrometer equipped with a E-231 TE-102 rectangular cavity, and interfaced with an IBM personal computer for accumulation and digitization of the spectra. The sample temperature was controlled by variable temperature helium flow cryostat system (Oxford Instruments). EPR spectra of the compound were taken at several temperatures: 4.2, 10, 30, 50, 77, 173, and 200 K.

The EPR spectrum of the frozen Mn—Me$_2$BBZ complex (FIG. 9) shows six sharp lines centered at g=2 characteristic of a high spin Mn(II) ion with a small zero-field splitting. As expected, only the transitions within the $m_s$=−½ ⟵⟶ $m_s$=+½ manifold are observed. The observed nuclear hyperfine splitting is typical of a high spin manganese ion (|A|=95±1 G).

Above 173 K, the hyperfine components are broadened due to relaxation effects. However, at temperatures lower than 173 K, the spectrum sharpens to reveal lines of lower intensity between the major transitions are resolved. These smaller transitions are in the correct field positions to be assigned to the $\Delta m_s=+1$, $\Delta m_I=\pm 1$ forbidden transitions, and all ten expected transitions are discerned. These spectral features are indicative of a nearly cubic environment for the high spin Mn(II) ion, which is consistent with the out-of-plane distortion of the metal from the mean ligand plane.

Figure 9:
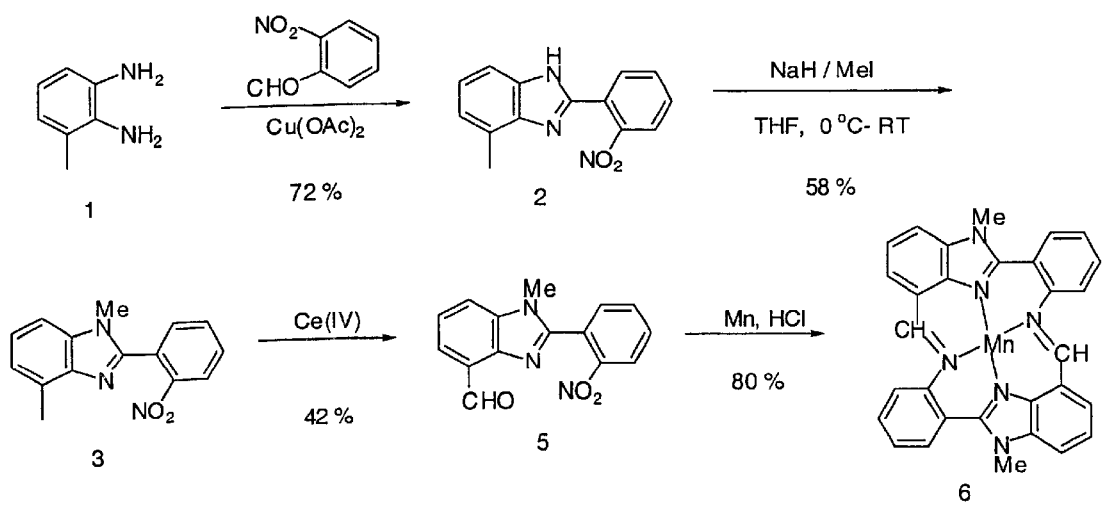
FIG. 9 is an EPR spectra of [Mn(Me$_2$BBZ)Cl]Cl (9): (a) experimental data (solid line) and the calculated spectrum (dashed line) simulated without inclusion of second order effect on transition probabilities and forbidden transitions with |A|=95 G and |D|=105 G. (b) experimental data (solid line) and the fully simulated spectra (dashed line) computed with the same |A| and |D| values as (a).

The value of D, the axial splitting parameter, may be estimated from the intensity of the transitions.[18] Another method involves analysis of the intensity ratios of the allowed transitions.[19] An upper limit of 150–200 Gauss or 0.015–0.02 cm$^{-1}$ was estimated for D by this procedure. A more reliable determination was obtained by spectral simulation using the program EPR-NMR (Department of Chemistry, University of Saskatchewan, Canada). In this manner, the observed spectrum could be simulated to best fit both the positions and intensities of the forbidden lines. We obtained $|A|=95$ Gauss and $D=0.01$ cm$^{-1}$ from these simulations. The calculated EPR spectrum using these values show good agreement to the experimental data (FIG. 9).

Temperature-Dependent Magnetization Measurements of the Mn—Me$_2$BBZ complex Field- and temperature-dependent magnetization measurements were performed on a Quantum Design MPMS Squid Magnetometer. Samples were held in either gel capsule or delrin screw-cap holders. The diamagnetic correction of the sample and holder, $\chi_{dia}$, was determined from a plot of the measured magnetic susceptibility, $\chi_{obs}$, vs. inverse temperature. The correction may be estimated from the intercept upon extrapolation to infinite temperature. The magnetization of the sample was measured between 0 and 55 kG at constant temperature (1.9 K). The variable-temperature behavior was determined between 2 and 300 K at constant field (500 G). The data were fitted to Curie-Weiss law, $\chi_m=C/(T-\theta)$, where $\chi_m$ is the molar magnetic susceptibility. $\theta$ has the units of temperature (K) and is obtained empirically from the plot of $\chi_m^{-1}$ vs. T. The spin of the system (S) was calculated from the susceptibility ($\chi_m= Ng^2\mu_B^2 S(S+1)/3$ $kT=N\mu_{eff}^2/3$ kT).

Figure 10:
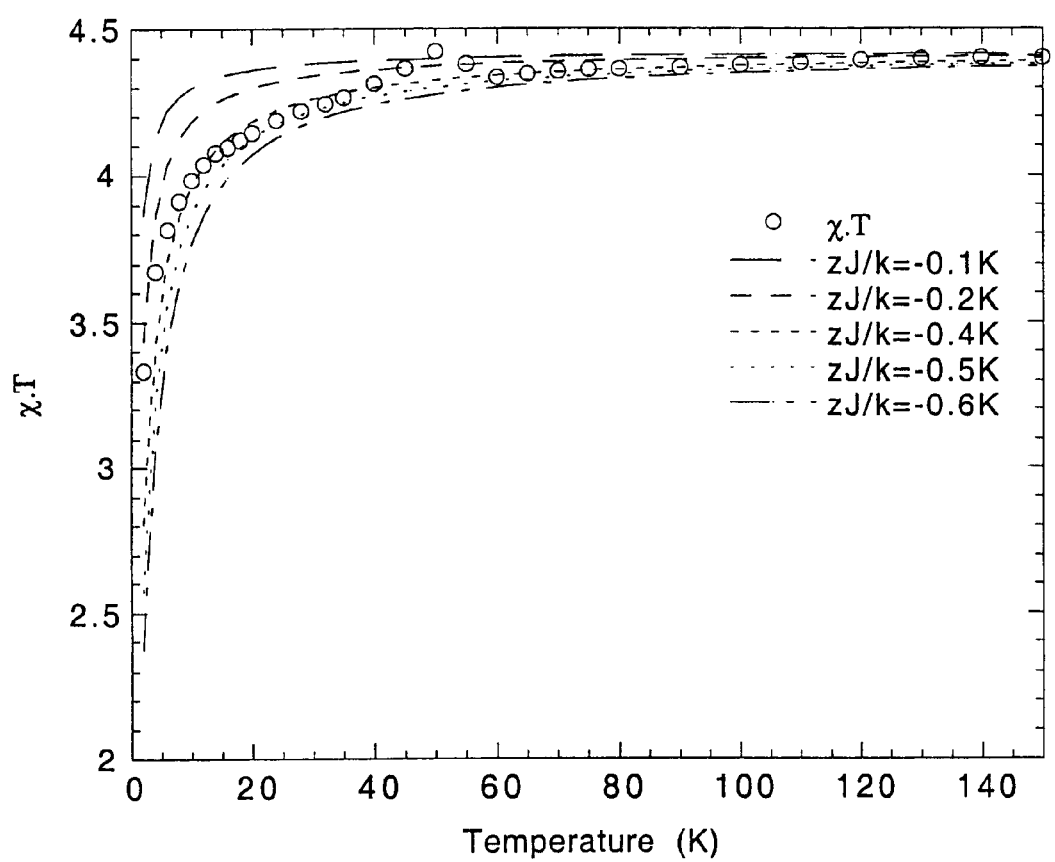
FIG. 10 is a comparison of magnetic susceptibility data (open circle) and the calculated susceptibility curves calculated using Eqs. (1–9) with various zJ/k values (–0.1~–0.6 K).

The experimental data are shown in FIG. 10. At room temperature, $S\sim 2.5$ and $\mu_{eff}=5.96$, consistent with a high-spin Mn(II) ion. The Curie constant (C) and Weiss correction ($\theta$) obtained are 4.47 and $-0.97$, respectively. The negative $\theta$ provides a measure of the zero-field splitting (D) and the near-neighbor superexchange interactions (J).

Following earlier work, the susceptibility data were fitted using a model proposed by Watanabe[20] and McElearney et al.[21], in which the intermolecular exchange interactions were treated as a perturbing molecular field. First, we write the total spin Hamiltonian of a single ion as $$H=g\beta S_z H-DS_z^2 \tag{1}$$

The energy levels for the ion for different orientations of the magnetic field along the molecular x, y, z axes can be readily calculated. Using these results, we obtain the following expressions for the anisotropic magnetic susceptibility:

$$\chi_\| = \frac{2Ng^2\mu_B^2}{kT}\frac{1+9e^{-2D/kT}+\frac{25e^{-6D/kT}}{(1+e^{-2D/kT}+e^{-6D/kT})}} \tag{2}$$

$$\chi_\perp = \frac{2Ng^2\mu_B^2}{kT}9+8kT/D-11kT/2De^{-2D/kT}-\frac{5kT/De^{-6D/kT}}{(1+e^{-2D/kT}+e^{-6D/kT})} \tag{3}$$

For high-spin Mn(II), the molecular g-values are isotropic. The molecular exchange field is then introduced by adding an exchange term into the spin Hamiltonian. In the mean field approximation $2\Re_j J_{ij} S_i \cdot S_j$ is replaced by $A \cdot S<S>$, the thermal equilibrium approximation and A is the molecular field coefficient. The relation between $A \cdot S<S>$ and $2\Re_j J_{ij} S_i \cdot S_j$ is $$-2\Sigma_j J_{ij} S_i \cdot S_j \approx -2zJS \cdot <S>=AS \cdot <S>, \tag{4}$$

where, $-2zJ=A$, and z and J denote the number of nearest neighbors and the exchange integral, respectively. The molecular exchange field is then $$H' = \frac{2zJ}{Ng^2\mu_B^2}\chi_i' H_i, i = \|, \perp, \tag{5}$$

where $\chi_i'$ is the exchange-corrected susceptibility actually measured and where $H_i$ denotes the external field. The resulting exchange fields are assumed to be collinear.

Thus there is additional field turned on in the presence of the applied or measuring field. Accordingly, $$M_i=\chi_i(H_i+H_i'). \tag{6}$$

By definition the measured susceptibility is given by $$\chi_i' = \lim_{H_i \to 0} \frac{M_i}{H_i}, \tag{7}$$

The exchange-corrected susceptibility is then given by [combining Eqs. (5–7)]

$$\chi_i' = \frac{\chi_i}{1-(2zJ/Ng^2\mu_B^2)\chi_i}. \tag{8}$$

For powder samples, we obtain $$\chi_{powder}=(2\chi_\perp'+\chi_\|')/3. \tag{9}$$

FIGS. 10 shows the fit to the experimental data in the form of $\chi_{powder}$T vs. temperature plots. For the best fit, $J/k=0.4$ K (0.278 cm$^{-1}$) and $D/k=0.01$ K (0.007 cm$^{-1}$). From these two results, it is clear that the value of J has more significant effect on the susceptibility data than the zero-field splitting. In fact, a wide range of D values fit the data fairly well (0.01–1K), indicating that the zero-field terms cannot account for the observed magnetic features. Ginsberg et. al.[22] have noted a similar zero-field independent magnetic susceptibility for dimeric system with intramolecular antiferromagnetic exchange interaction.

From the sign of J, the exchange interaction is also antiferromagnetic in the present case. While the weak antiferromagnetic coupling determined from these measurements would not be favorable towards the preparation of ferrimagnetic materials, these data do support the notion that the "staircase" motif can mediate weak electronic and magnetic interactions. The sign of these exchange coupled interactions (ferro- or antiferromagnetic) could be dependent on subtle alterations at the metal center (i.e. metal species, extent of ruffling, symmetry of the metal environment). Further studies of other related complexes should help to elucidate the factors that modulate the nature of these intermolecular couplings.

Synthesis Scheme 2

Figure 11:
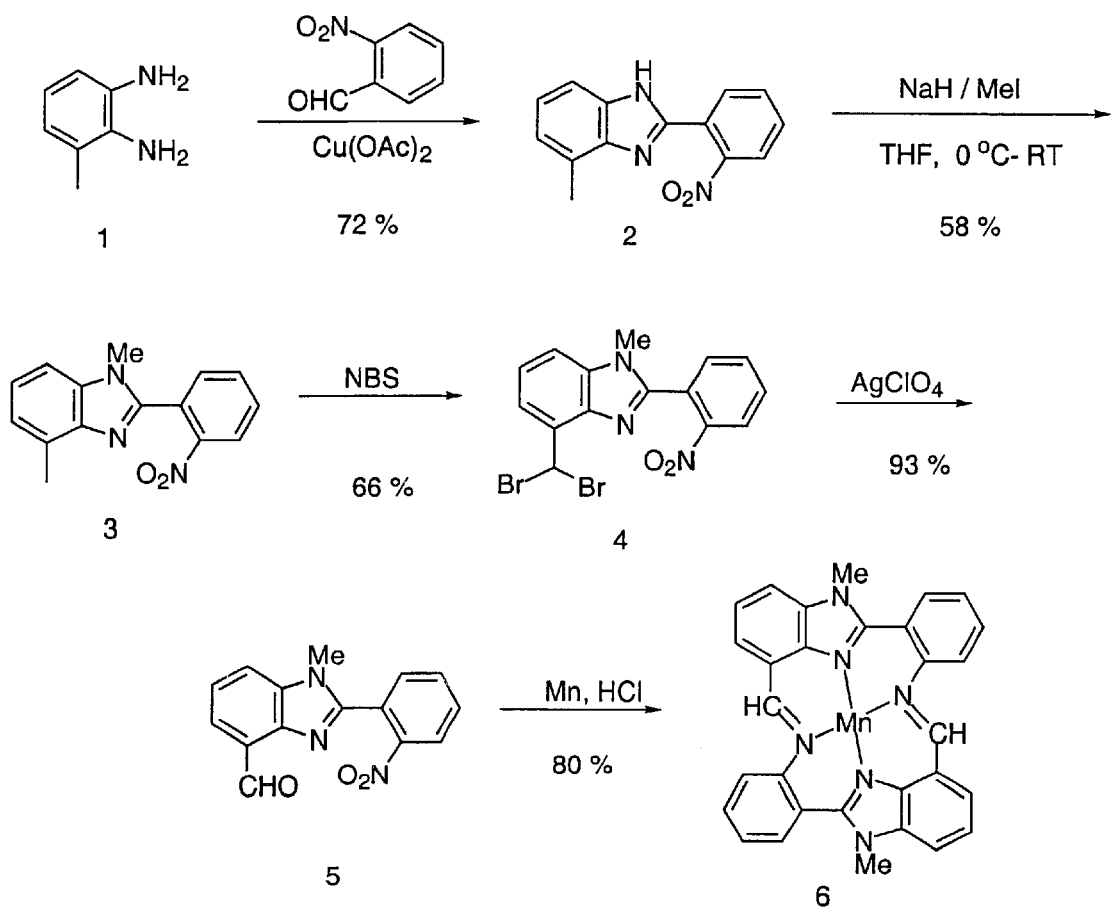
FIG. 11 shows another synthetic scheme for the synthesis of Me$_2$BBZ ligand and its associated manganese complex.

A second procedure or synthetic scheme for making BBZ ligands and their related metal complexes is shown in FIG. 11. The specific protocol used to prepare the manganese BBZ complex is as follows:

Unless otherwise noted, all materials were obtained from commercial suppliers and used without further purification. Thin layer chromatography was performed on Whatman precoated silica gel $UV_{254}$ plates. Silica gel (32–63 m) was used for column chromatography.

4-Methyl-2-(2-nitrophenyl)-benzimidazole (2)

2,3-Diaminotoluene (12.2 g, 0.1 mol) was dissolved in the mixture of $MeOH/H_2O$ (500 mL, v/v=1:1), acetic acid (10 mL) was added to the stirring mixture. 2-Nitrobenzaldehyde (21.1 g, 0.14 mol) in MeOH (250 mL) and $Cu(OAc)_2.H_2O$ (28.0 g, 0.14 mmol) in water (250 mL) were added subsequentially to the mixture. It was then heated to reflux for 3 h under vigously stirring, a pale yellow precipitate was formed. Filtered while it was hot and washed with water to afford a gray-yellow solid. Redissolved the precipitate in EtOH (600 mL) and HCl (75 ML, Conc.), a solution of $Na_2S.9 H_2O$ (48.0 g, 0.2 mol) in water (300 mL) were added. The mixture was heated to reflux for 1 h resulted in a black slurry. Cooled down to room temperature, it was filtered through a pad of celite to remove of CuS. The filtrate was neutralized with ammonium hydroxide to PH=8–9. Concentration using a rotary evaporator, a green-yellow precipitate was formed. After filtration and dried in vaccum oven, the crude product was purified by column chromatography on silica gel using a mixture of hexane/ethyl acetate (1:1) as the eluent to give 4-methyl-2-(2-nitrophenyl)-benzimidazole (18 g, 72%) as a yellow needle crystal. $R_f$=0.21 (hexane/ethyl acetate=1:1); $^1H$ NMR (250 MHz, $CDCl_3$) δ 2.60 (s, 3H), 7.10 (d, J=8.2 Hz, 1H), 7.20 (t, J=7.9 Hz, 1H), 7.41 (bs, 1H), 7.52–7.66(m, 2H), 7.89–7.97 (m, 2H), 10.41 (bs, 1H); HRMS: Calcd for $C_{14}H_{11}N_3O_2$ 253.0851, found 253.0854.

N-Methyl-4-methyl-2-(2-nitrophenyl)-benzimidazole (3)

A solution 4-methyl-2-(2-nitrophenyl)-benzimidazole (5.06 g, 20 mmol) in THF (50 mL) was added to a stirring suspension of NaH (1.2 g, 60% dispersion in mineral oil, 30 mmol) in THF (50 mL) at 0° C. under $N_2$. The mixture was stirred at 0° C. for 30 min. and was then allowed to warm to r.t. for 1 h to form a orange solution. MeI (8.52 g, 60 mmol) was transfered into the above mixture dropwisely by a cannular at r.t under $N_2$. This mixture was stirred for 24 h under $N_2$ to result in a pale yellow solution. Saturated $NaHCO_3$ (100 mL) was added. The water layer was extracted with $CHCl_3$, the combined extracts was washed with brine, dried over $Na_2SO_4$. After removing of solvent, the residue was purified by column chromatography on silica gel using a mixture of hexane/ethyl acetate (1:1) as the eluent to give N-methyl-4-methyl-2-(2-nitrophenyl)-benzimidazole (3.0 g, 58%) as a yellow needle crystal. $R_f$=0.21 (hexane/ethyl acetate 1:1); $^1H$ NMR (300 MHz, $CDCl_3$) δ 2.68 (s, 3H), 3.60 (s, 3H), 7.12 (m, 1H), 7.26 (m, 2H), 7.65–7.80 (m, 3H), 8.23 (d, J=7.9 Hz, 1H). HRMS: Calcd for $C_{15}H_{13}N_3O_2$ 267.1007, found 267.1007.

4-Dibromomethyl-N-methyl-2-(2-nitrophenyl)-benzimidazole (4)

N-Methyl-4-methyl-2-(2-nitrophenyl)-benzimidazole (86 mg, 0.32 mmol) was dissolved in the minimum amount of $CHCl_3$, carbon tetrachloride (5 mL) and N-bromosuccinimide (172 g, 0.96 mmol) were added to the mixture. The mixture was refluxed under irradiation with a sunlamp for 8 hours. After cooling with ice-water bath, the succinimide was filtered off and the filtrate was washed with saturated $Na_2S_2O_3$, brine, dried over $Na_2SO_4$. After removing of solvent, the residue was purified by column chromatography on silica gel using a mixture of hexane/ethyl acetate (1:1) as the eluent to afford 4-dibromomethyl-N-methyl-2-(2-nitrophenyl)-benzimidazole (91 mg, 66%) as a light yellow crystal. $R_f$=0.21 (hexane/ethyl acetate 1:1); $^1H$ NMR (250 MHz, $CDCl_3$) δ 3.61 (s, 3H), 7.35–7.47 (m, 2H), 7.59 (s, 1H), 7.69 (dd, $J_{1=7.4}$ Hz, $J_2$=7.4 Hz, $J_2$=1.8 Hz, 1H), 7.74–7.86 (m, 3H), 8.25 (dd, $J_1$=7.8 Hz, $J_2$ =1.8 Hz, 1H). HRMS: Calcd for $C_{15}H_{11}Br_2N_3O_2$ 422.9217, found 422.9211.

N-Methyl-2-(2-nitrophenyl)-benzimidazole-4-benzaldehyde (5)

A solution of silver hyperchlorate (57 mg, 0.27 mmol) in water (2 mL) was added to a solution of 4-dibromomethyl-N-methyl-2-(2-nitrophenyl)-benzimidazole (39 mg, 0.9 mmol) in 1,4-dioxane (2 mL). The mixture was refluxed for 5 h to afford a grey suspension. After cooling to room temperature, the precipitate was filtered off through a pad of celite and washed with ethyl acetate. The filtrate was washed with water and brine, dried over $Na_2SO_4$. Concentration using a rotary evaporator and subsequent column chromatography on silica gel using hexane/ethyl acetate (1:3) as the eluent to give N-methyl-2-(2-nitrophenyl)-benzimidazole-4-benzaldehyde (24 g, 93%) as a light-yellow solid. $R_f$=0.23 (hexane/ethyl acetate=1:3); $^1H$ NMR (250 MHz, $CDCl_3$) δ 3.68 (s, 3H), 7.47 (t, J=7.8 Hz, 1H), 7.66–7.74 (m, 2H), 7.77–7.86 (m, 2H). 7.90 (d, J=7.6 Hz, 1H), 8.28 (dd, J,=7.9 Hz, $J_2$ =1.5 Hz, 1H), 10.81 (s, 1H). HRMS: Calcd for $C_1H_{11}N_3O_3$ 281.0800, found 281.0814.

Synthesis of $Mn(BBZ)Cl_2$ (6)

Manganese powder (0.298 g, 5.42 mmol), water (0.50 mL), HCl (10 µL, 12 N) were added consecutively to a solution of 5 (75 mg, 0.25 mmol) in ethanol (5 mL). After refluxing the mixture for 2 hr, the reaction mixture was filtered hot. Following an ethanol wash, the filtrates were combined and the solvent was removed in vacuo. The crude product was titurated with ethyl acetate and it was filtered and dried to give 59.7 mg (80%) of the title compound.
Synthesis Scheme 3

Figure 12:
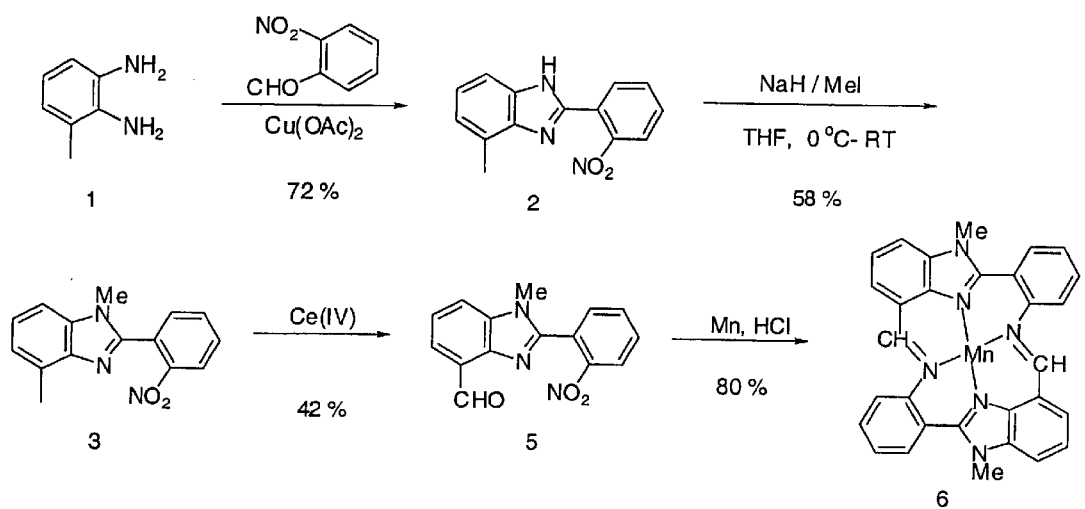
FIG. 12 shows still another scheme for synthesizing Me$_2$BBZ ligands and their associated manganese complexes in accordance with the present invention.

A third procedure or synthetic scheme for making BBZ ligands and their related metal complexes is shown in FIG. 12. The specific protocol used to prepare the manganese BBZ complex is as follows:

Unless otherwise noted, all materials were obtained from commercial suppliers and used without further purification. Thin layer chromatography was performed on Whatman precoated silica gel $UV_{254}$ plates. Silica gel (32–63 m) was used for column chromatography.

4-Methyl-2-(2-nitrophenyl)-benzimidazole (2)

2,3-Diaminotoluene (12.2 g, 0.1 mol) was dissolved in the mixture of $MeOH/H_2O$ (500 mL, v/v=1:1), acetic acid (10 mL) was added to the stirring mixture. 2-Nitrobenzaldehyde (21.1 g, 0.14 mol) in MeOH (250 mL) and $Cu(OAc)_2H_2O$ (28.0 g, 0.14 mmol) in water (250 mL) were added subsequentially to the mixture. It was then heated to reflux for 3 h under vigously stirring, a pale yellow precipitate was formed. Filtered while it was hot and washed with water to afford a gray-yellow solid. Redissolved the precipitate in EtOH (600 mL) and HCl (75 mL, Conc.), a solution of $Na_2S.9 H_2O$ (48.0 g, 0.2 mol) in water (300 mL) were added. The mixture was heated to reflux for 1 h resulted in a black slurry. Cooled down to room temperature, it was filtered through a pad of celite to remove of CuS. The filtrate was neutralized with ammonium hydroxide to PH=8–9. Concentration using a rotary evaporator, a green-yellow precipitate was formed. After filtration and dried in vaccum oven, the crude product was purified by column chromatography on silica gel using a mixture of hexane/ethyl acetate (1:1) as the eluent to give 4-methyl-2-(2-nitrophenyl)-benzimidazole (18 g, 72%) as a yellow needle crystal. $R_f$=0.21 (hexane/ethyl acetate=1:1); $^1$H NMR (250 MHz, CDCl$_3$) δ 2.60 (s, 3H), 7.10 (d, J=8.2 Hz, 1H), 7.20 (t, J=7.9 Hz, 1H), 7.41 (bs, 1H), 7.52–7.66(m, 2H), 7.89–7.97 (m, 2H), 10.41 (bs, 1H); HRMS: Calcd for $C_{14}H_{11}N_3O_2$ 253.0851, found 253.0854.

N-Methyl-4-methyl-2-(2-nitrophenyl)-benzimidazole (3)

A solution 4-methyl-2-(2-nitrophenyl)-benzimidazole (5.06 g, 20 mmol) in THF (50 mL) was added to a stirring suspension of NaH (1.2 g, 60% dispersion in mineral oil, 30 mmol) in THF (50 mL) at 0° C. under $N_2$. The mixture was stirred at 0° C. for 30 min. and was then allowed to warm to r.t for 1 h to form a orange solution. MeI (8.52 g, 60 mmol) was transfered into the above mixture dropwisely by a cannular at r.t under $N_2$. This mixture was stirred for 24 h under $N_2$ to result in a pale yellow solution. Saturated NaHCO$_3$ (100 mL) was added. The water layer was extracted with CHCl$_3$, the combined extracts was washed with brine, dried over Na$_2$SO$_4$. After removing of solvent, the residue was purified by column chromatography on silica gel using a mixture of hexane/ethyl acetate (1:1) as the eluent to give N-methyl-4-methyl-2-(2-nitrophenyl)-benzimidazole (3.0 g, 58%) as a yellow needle crystal. $R_f$=0.21 (hexane/ethyl acetate 1:1); $^1$H NMR (300 MHz, CDCl$_3$) δ 2.68 (s, 3H), 3.60 (s, 3H), 7.12 (m, 1H), 7.26 (m, 2H), 7.65–7.80 (m, 3H), 8.23 (d, J=7.9 Hz, 1H). HRMS: Calcd for $C_{15}H_{13}N_3O_2$ 267.1007, found 267.1007.

N-Methyl-2-(2-nitrophenyl)-benzimidazole-4-benzaldehyde (4)

A solution of ceric ammonium nitrate (2.19 g, 4.0 mmol) in acetic acid (10 mL, 50%) was added to a stirred solution of N-methyl-4-methyl-2-(2-nitrophenyl)-benzimidazole (0.27 g, 1.0 mmol) in same acid (5.0 mL, 50%) dropwise at 90° C. and the mixture was stirred for 6 hours. The mixture was then cooled to room temperature, neutralized with saturated NaHCO$_3$ to PH=7–8,extracted with CHCl$_3$ and the extract dried over Na$_2$SO$_4$. Concentration using a rotary evaporator and subsequent column chromatography on silica gel using hexane/ethyl acetate (1:3) as the eluent to give N-methyl-2-(2-nitrophenyl)-benzimidazole-4-benzaldehyde (115 mg, 42%) as a light-yellow solid. $R_f$=0.28 (hexane/ethyl acetate=1:3); $^1$H NMR (250 MHz, CDCl$_3$) δ 3.68 (s, 3H), 7.47 (t, J=7.8 Hz, 1H), 7.66–7.74 (m, 2H), 7.77–7.86 (m, 2H), 7.90 (d, J=7.6 Hz, 1H), 8.28 (dd, J,=7.9 Hz, J$_2$ =1.5 Hz, 1H), 10.81 (s, 1H). HRMS: Calcd for $C_{15}H_{11}N_3O_3$ 281.0800, found 281.0814.

Synthesis of Mn(BBZ)Cl$_2$ (5)

Manganese powder (0.298 g, 5.42 mmol), water (0.50 mL), HCl (10 μL, 12 N) were added consecutively to a solution of 6 (75 mg, 0.25 mmol) in ethanol (5 mL). After refluxing the mixture for 2 hr, the reaction mixture was filtered hot. Following an ethanol wash, the filtrates were combined and the solvent was removed in vacuo. The crude product was titurated with ethyl acetate and it was filtered and dried to give 59.7 mg (80%) of the title compound.

Figure 13:
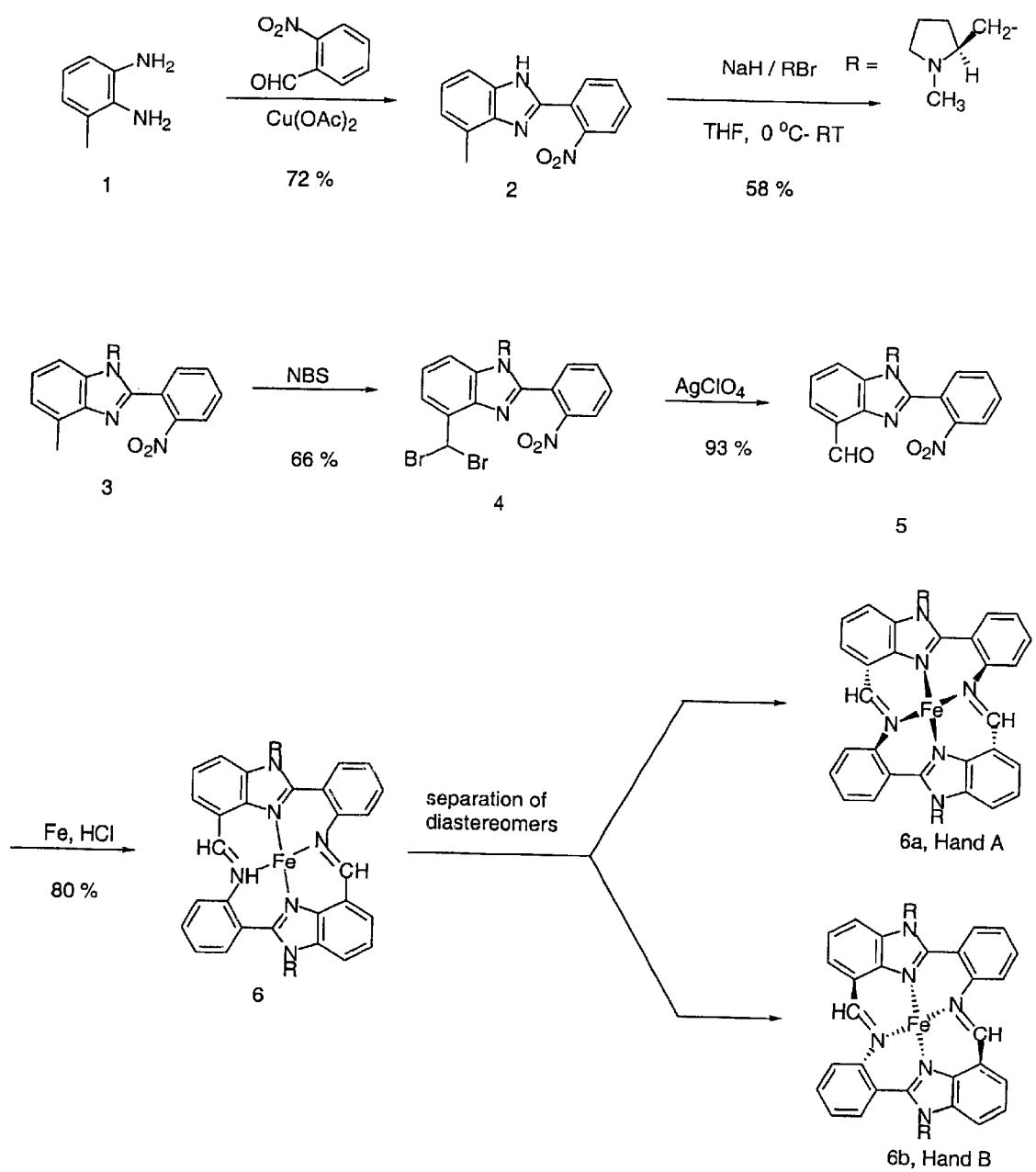
FIGS. 13 and 14 illustrate two different approaches to synthesizing chiral bis benzimidazoles substituted with (S)-(–)-methyl-2-pyrrolidine methyl at their benzimidazole nitrogens.

Synthesis of Chiral Bis Benzimidazoles Substituted with (S)-(–)-methyl-2-pyrrolidine methyl at the Benzimidazole Nitrogens FIG. 13 illustrates one synthesis for these compounds. For this synthesis, 1H NMR spectra were recorded on a Bruker WM 250 (250 MHz) spectrometer. Spectra were referenced internally to the residual proton resonance in CDC13 (d 7.26 ppm) as internal standard. Chemical shifts (d) were reported as part per million (ppm) in d scale. Coupling constant (J) were reported in Hertz (Hz). NMR spectroscopic terms are reported by using the following abbreviations: s, single; d, double; t, triplet; m, multiplet.

Unless otherwise noted, all materials were obtained from commercial suppliers and used without further purification. Thin layer chromatography was performed on Whatman precoated silica gel UV254 plates. Silica gel (32–63m) was used for column chromatography.

4-Methyl-2-(2-nitrophenyl)-benzimidazole (2)

2,3-Diaminotoluene (12.2 g, 0.1 mol) was dissolved in the mixture of MeOH/H$_2$O (500 mL, v/v=1:1), acetic acid (10 mL) was added to the stirring mixture. 2-Nitrobenzaldehyde (21.1 g, 0.14 mol) in MeOH (250 mL) and Cu(OAc)$_2$.H$_2$O (28.0 g, 0.14 mmol) in water (250 mL) were added subsequentially to the mixture. It was then heated to reflux for 3 h under vigously stirring, a pale yellow precipitate was formed. Filtered while it was hot and washed with water to afford a gray-yellow solid. Redissolved the precipitate in EtOH (600 mL) and HCl (75 mL, Conc.), a solution of Na$_2$.S9 H$_2$O (48.0 g, 0.2 mol) in water (300 mL) were added. The mixture was heated to reflux for 1 h resulted in a black slurry. Cooled down to room temperature, it was filtered through a pad of celite to remove of CuS. The filtrate was neutralized with ammonium hydroxide to PH=8–9. Concentration using a rotary evaporator, a green-yellow precipitate was formed. After filtration and dried in vaccum oven, the crude product was purified by column chromatography on silica gel using a mixture of hexane/ethyl acetate (1:1) as the eluent to give 4-methyl-2-(2-nitrophenyl)-benzimidazole (18 g, 72%) as a yellow needle crystal. $R_f$=0.21 (hexane/ethyl acetate=1:1); $^1$H NMR (250 MHz, CDCl$_3$) δ 2.60 (s, 3H), 7.10 (d, J=8.2 Hz, 1H), 7.20 (t, J=7.9 Hz, 1H), 7.41 (bs, 1H), 7.52–7.66(m, 2H), 7.89–7.97 (m, 2H), 10.41 (bs, 1H); HRMS: Calcd for $C_{14}H_{11}N_3O_2$ 253.0851, found 253.0854.

N-((S)-(–)-1-Methyl-2-pyrrolidine-methyl)-4-methyl-2-(2-nitrophenyl)-benzimidazole (3)

A solution 4-methyl-2-(2-nitrophenyl)-benzimidazole (5.06 g, 20 mmol) in THF (50 mL) was added to a stirring suspension of NaH (1.2 g, 60% dispersion in mineral oil, 30 mmol) in THF (50 mL) at 0° C. under $N_2$. The mixture was stirred at 0° C. for 30 min. and was then allowed to warm to r.t for 1 h to form a orange solution. (S)-(–)-1-Methyl-2-pyrrolidinemethyl bromide (10.74 g, 60 mmol) was transferred into the above mixture dropwise by canula at r.t under N2. This mixture was stirred for 24 h under N2 to result in a pale yellow solution. Saturated NaHCO$_3$ (100 mL) was added. The water layer was extracted with CHCl3,the combined extracts was washed with brine, dried over Na$_2$SO$_4$. After removing of solvent, the residue was purified by column chromatography on silica gel using a mixture of hexane/ethyl acetate (1:1) as the eluent to give N-((S)-(–)-1-methyl-2-pyrrolidine-methyl)-4-methyl-2-(2-nitrophenyl)-benzimidazole (3.58 g, 58%).

4-Dibromomethyl-N-((S)-(–)-1-methyl-2-pyrrolidine-methyl)-2-(2-nitrophenyl)-benzimidazole (4)

N-((S)-(–)-1-methyl-2-pyrrolidine-methyl)-4-methyl-2-(2-nitrophenyl)-benzimidazole (113.52 mg, 0.32 mmol) was dissolved in the minimum amount of CHCl₃, carbon tetrachloride (5 mnL) and N-bromosuccinimide (172 g, 0.96 mmol) were added to the mixture. The mixture was refluxed under irradiation with a sunlamp for 8 hours. After cooling with ice-water bath, the succinimide was filtered off and the filtrate was washed with saturated $Na_2S_2O_3$, brine, dried over $Na_2SO_4$. After removing of solvent, the residue was purified by column chromatography on silica gel using a mixture of hexane/ethyl acetate (1:1) as the eluent to afford 4-dibromomethyl-N-methyl-2-(2-nitrophenyl)-benzimidazole.

N-((S)-(−)-1-methyl-2-pyrrolidine-methyl)-2-(2-nitrophenyl)-benzimidazole-4-benzaldehyde (5)

A solution of silver hyperchlorate (57 mg, 0.27 mmol) in water (2 ml) was added to a solution of 4-dibromomethyl-N-((S)-(−)-1-methyl-2-pyrrolidine-methyl)-2-(2-nitrophenyl)-benzimidazole (46 mg, 0.9 mmol) in 1,4-dioxane (2 ml). The mixture was refluxed for 5 h to afford a gray suspension. After cooling to room temperature, the precipitate was filtered off through a pad of celite and washed with ethyl acetate. The filtrate was washed with water and brine, dried over $Na_2SO_4$. Concentration using a rotary evaporator and subsequent column chromatography on silica gel using hexane/ethyl acetate (1:3) as the eluent to give N-((S)-(−)-1-methyl-2-pyrrolidine-methyl)-2-(2-nitrophenyl)-benzimidazole-4-benzaldehyde.

Synthesis of Fe(MPM-BBZ)Cl₂ (6a,b)

Iron powder (0.298 g, 5.42 mmol), water (0.50 mL), HCl (10 μL, 12 N) were added consecutively to a solution of 6 (85 mg, 0.25 mmol) in ethanol (5 ml). After refluxing the mixture for 2 hr, the reaction mixture was filtered hot. Following an ethanol wash, the filtrates were combined and the solvent was removed in vacuo. The crude product was triturated with ethyl acetate and it was filtered and dried to give the title compound. Two diastereomers of the iron complex were separated on silica by standard chromatography.

Figure 14:
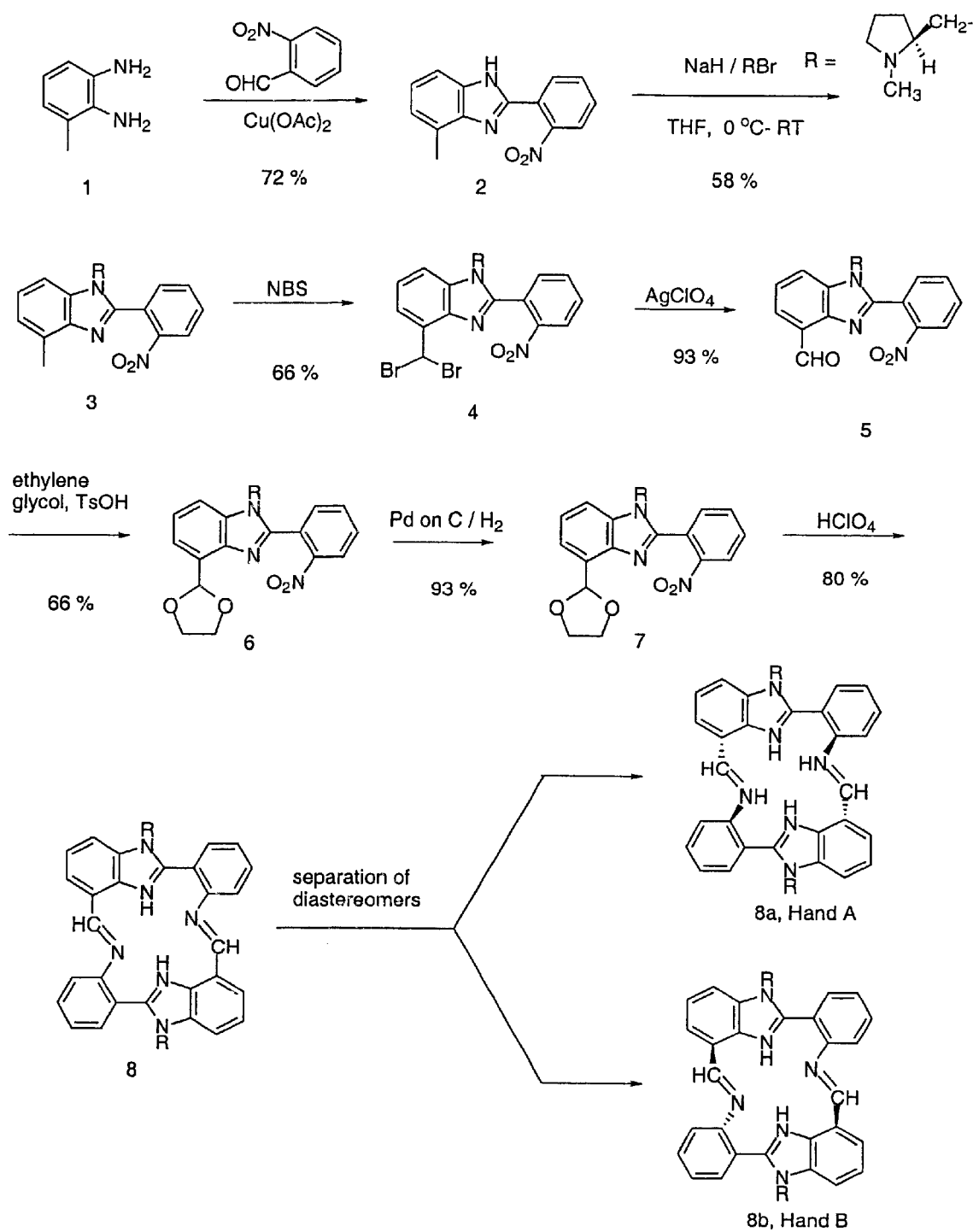

Alternative Synthesis for Chiral Bis Benzimidazoles Substituted with (S)-(−)-methyl-2-pyrrolidine methyl at the Benzimidazole Nitrogens This synthesis is illustrated in FIG. 14.

N-((S)-(−)-1-methyl-2-pyrrolidine-methyl)-2-(2-nitrophenyl)-benzimidazole-4-benzaldehyde ethylene acetal (6)

N-((S)-(−)-1-methyl-2-pyrrolidine-methyl)-2-(2-nitrophenyl)-benzimidazole-4-carboxaldehyde 5 (6.27 g, 23.5 mmol) was dissolved in benzene (150 mL), and mixed with ethylene glycol (6.5 mL, 118 mmol) and p-toluenesulfonic acid monohydrate (0.450 g, 2.35 mmol). The mixture was heated to reflux overnight and the water was removed by azeotropic distillation. The resulting solution was allowed to cool to room temperature, and was then neutralized with saturated $NaHCO_3$, washed with water and brine and dried over $Na_2SO_4$. The compound was purified by column chromatography on silica gel using hexane/ethyl acetate (1:2) as the eluent to give 2-(2-nitrophenyl)-benzimidazole-4-carboxaldehyde ethylene acetal as a yellow solid.

N-((S)-(−)-1-methyl-2-pyrrolidine-methyl)-2-(2-aminophenyl)-benzimidazole-4-carboxaldehyde ethylene acetal (7)

A solution of 6 (0.85 g, 2.6 mmol) in 50 mL MeOH was mixed with 85 mg of Pd/C and hydrogenated with $H_2$ at a pressure of 10 psi for 3 hours. The mixture was then filtered, and the solvent was removed to give the title compound as a white solid.

[H₂(MPM₂BBZ)](ClO₄)₂ (8a, 8b)

N-((S)-(−)-1-methyl-2-pyrrolidine-methyl)-benzimidazole-4-carboxaldehyde ethylene acetal (7) (0.62 g, 2.1 mmol) was dissolved in CH₃CN (15 mL) at room temperature, and then perchloric acid (0.42 mL, 2.3 mmol) was added. The mixture was stirred at room temperature for 2 days to yield a white suspension. It was then filtered to give the title compound as a white powder. The two diastereomers of the title compound could be separated by standard chromatography. The associated metal complexes complexes could be prepared by refluxing the unpurified free Me₂BBZ ligand with an equimolar amount of the divalent metal salt.

Synthesis of Me₂BBZ Complexes of Other Transition Metals

[Fe(Me₂BBZ)Cl](BPh₄)

A red-colored solution was obtained by refluxing 0.50 g (0.93 mmol) of the Me₂BBZ ligand ([H₂(Me₂BBZ)](ClO₄)) with FeCl₂.4H₂O (0.18 g, 0.93 mmol) in CH₃CN for 20 hrs under nitrogen. The solvent was removed in vacuo, and the resulting red solid was dissolved in 50 mL degassed MeOH. Addition of NaBPh₄ (0.31 g, 0.93 mmol) to the solution yielded a brick-red solid upon stirring for 15 minutes. Recrystallization from acetonitrile affords a dark brown solid (0.79 g, 85%). Crystals suitable for X-ray analysis were obtained by slow diffusion of pentane into an acetonitrile solution of the complex at −7° C. over a period of 3 days. Anal. Calcd. for [Fe(Me₂BBZ)Cl](BPh₄), $C_{54}H_{42}N_6BClFe$: C, 73.96; H, 4.79; N, 9.58; Found: C, 73.69; H, 4.76; N, 9.64. UV-visible spectrum ($\lambda(\epsilon, M^{-1} cm^{-1})$ in CH₃CN): 243 (2.17×10⁴), 328 (1.36×10⁴). IR (KBr, cm⁻¹) 1658w, 1609m, 1569m, 1519w, 1473s, 1427m, 1379m, 1222w, 1065w, 1030w, 848w, 810w, 734s, 704vs, 611m.

[Co(Me₂BBZ)Cl]Cl

The Me₂BBZ ligand (0.201 g, 0.43 mmol) was reacted with CoCl₂.6H₂O (0.13 g, 0.43 mmol) in CH₃CN. An orange red mixture was obtained upon stirring. The solution was refluxed for 20 hours and the solvent was removed by rotary evaporation. The crude product was purified by column chromatography (CH₂Cl₂:Hexane:MeOH=3:1:1) and dried to give an orange solid (0.201 g, 67.5% yield). Crystals suitable for X-ray analysis were obtained by slow diffusion of pentane into a methanol solution over 7 days at −7° C. Anal. Calcd. for [Co(Me₂BBZ)Cl]Cl, $C_{30}H_{22}N_6Cl_2Co$: C, 60.42; H, 43.69 , N 14.09; Found: C, 59.92; H, 3.83; N, 13.85. UV-visible spectrum ($\lambda(\epsilon, M^{-1} cm^{-1})$ in CH₃CN): 242 (2.76×10⁴), 328 (2.92×10⁴). IR (KBr, cm⁻¹) 1611s, 1570s, 1518w, 1473vs, 1429m, 1379m, 1301w, 1222m, 1189m, 1120w, 1066w, 921w, 849w, 798w, 753s, 715w, 590w.

[Ni(Me₂BBZ)(H₂O)₂](ClO₄)₂

The Me₂BBZ ligand (0.49 g, 0.96 mmol) was reacted with Ni(ClO₄)₂ (0.348 g, 0.96 mmol) in CH₃CN. The color of the solution changed from green to orange upon stirring. The solution was refluxed for 20 hours and the solvent was removed by rotary evaporation. The crude product was purified by column chromatography using CH₃CN as the eluent and dried to give an orange solid (0.55 g, 69% yield). Crystals suitable for X-ray analysis were obtained by slow diffusion of hexane into an acetonitrile solution over 7 days at −7° C. Anal. Calcd. for [Ni(Me$_2$BBZ)(H$_2$O)$_2$](ClO$_4$)$_2$, C$_{30}$H$_{26}$N$_6$O$_{10}$Cl$_2$Ni: C, 47.39; H, 3.42; N, 11.05; Cl, 9.33: Found: C,47.25; H, 3.60; N, 10.85; Cl, 9.44. UV-visible spectrum ($\lambda$($\epsilon$, M$^{-1}$ cm$^{-1}$) in CH$_3$CN): 242 (1.89×10$^4$), 333 (2.39×10$^4$). IR (KBr, cm$^{-1}$) 3450s,br, 1611s, 1569s, 1525w, 1485vs, 1435m, 1398m, 1377m, 1312w, 1231w, 1194m, 1099vs,br, 923w, 852w, 817w, 799w, 777w, 757s, 715w, 625s.

[Cu(Me$_2$BBZ)(ClO$_4$)$_2$]

The Me$_2$BBZ ligand (0.44 g, 0.82 mmol) was reacted with Cu(ClO$_4$)$_2$ (0.304 g, 0.82 mmol) in CH$_3$CN. The color of the solution changed from orange-red to yellow-orange color upon stirring. The solution was refluxed for 20 hours and the solvent was removed by rotary evaporation. The crude product was purified by column chromatography using CH$_3$CN as the eluent and dried to give a red solid (0.51 g, 75% yield). Crystals suitable for X-ray analysis were obtained by slow diffusion of hexane into an acetonitrile solution over 4 days at −7° C. Anal. Calcd. for [Cu(Me$_2$BBZ)(ClO$_4$)$_2$], C$_{30}$H$_{22}$N$_6$O$_8$Cl$_2$Cu: C, 49.41; H, 3.01; N, 11.52; Cl, 9.74: Found: C,49.90; H, 3.04; N, 12.12; Cl, 9.17. UV-visible spectrum ($\lambda$($\epsilon$, M$^{-1}$ cm$^{-1}$) in CH$_3$CN): 239 (2.64×10$^4$), 333 (2.93×10$^4$). IR (KBr, cm$^{-1}$) 1658w, 1612s, 1564s, 1525w, 1480vs, 1435m, 1383m, 1315w, 1291w, 1251w, 1230w, 1194w, 1094vs,br, 927w, 855w, 817w, 804w, 777w, 758s, 713w, 624s.

Methods for Preparing Precursors

4-Methyl-2,1,3-benzothiadiazole

Thionyl chloride (166 g, 1.4 mol) was added to a solution of 2,3-diaminotoluene (71 g, 0.58 mol) in pyridine (430 mL) dropwise at a temperature below 45° C. Concentrated HCl (300 mL) was then added dropwise while care was taken to ensure that the reaction temperature did not exceed 65° C. After cooling to room temperature, the reaction mixture was subjected to a steam distillation. The light-yellow oil suspension in the water layer was extracted with diethyl ether. The combined extracts were washed with brine and dried over Na$_2$SO$_4$. After removal of the solvent by rotary evaporation, 4-methyl-2,1,3-benzothiadiazole was obtained as a light-yellow liquid in 92% (80.6 g) of yield. R$_f$=0.62 (hexane/ethyl acetate=3:1); $^1$H NMR (200 MHz, CDCl$_3$) $\delta$2.74 (s, 3H), 7.34 (m, 1H), 7.48 (d,J$_1$=8.7 Hz, J$_2$=6.7 Hz, 1H), 7.83 (m, 1H).

4-Bromomethyl-2,1,3-benzothiadiazole

A mixture of 4-methyl-2,1,3-benzothiadiazole (6.0 g, 40 mmol) and N-bromosuccinimide (7.12 g, 40 mmol) in carbon tetrachloride (80 mL) was refluxed under irradiation with a sunlamp for 8 hours. After cooling with ice-water bath, the succinimide was filtered off and the filtrate was washed with saturated Na$_2$S$_2$O$_3$, brine, dried over Na$_2$SO$_4$. After removal of solvent pure 4-bromomethyl-2,1,3-benzothiadiazole (8.8 g, 96%) was obtained as a light-yellow crystalline powder. R$_f$=0.45 (hexane/ethyl acetate= 4:1); $^1$H NMR (200 MHz, CDCl$_3$) $\delta$5.00 (s, 2H), 7.57 (m, 2H), 7.98 (d, J$_1$=8.5 Hz, J$_2$=1.2 Hz, 1H); HRMS: Calcd. for C$_7$H$_5$BrN$_2$S 227.9357, found 227.9395.

4-Hydroxymethyl-2,1,3-benzothiadiazole

A solution of silver perchlorate (4.75 g, 23 mmol) in water (10 mL) was added to a solution of 4-bromomethyl-2,1,3-benzothiadiazole (4.38 g, 19 mmol) in 1,4-dioxane. The mixture was refluxed for 4 hours to afford a light-yellow suspension. After cooling to room temperature, the precipitate was filtered off through a pad of celite and washed with CH$_2$Cl$_2$. The filtrate was washed with water and brine, dried over Na$_2$SO$_4$. Concentration using a rotary evaporator and subsequent column chromatography on silica gel using hexane/ethyl acetate (5:1) as the eluent afforded 4-hydroxymethyl-2,1,3-benzothiadiazole (2.0 g, 63%) as a light-yellow solid. R$_f$=0.23 (hexane/ethyl acetate=5:1); $^1$H NMR (200 MHz, CDCl$_3$) $\delta$2.73 (t,J=6.4 Hz, 1H), 5.18 (d,J=6.4 Hz, 2H), 7.58 (m, 2H), 7.94 (m, 1H); HRMS:Calcd. for C$_7$H$_6$N$_2$OS 166.0201, found 166.0219.

Using BBZ Ligand Metal Complexes to Catalyze Epoxidation Reactions

Catalytic Properties

Despite different oxidation couples between our [Mn(II)(Me$_2$BBZ)Cl]Cl complex and the more traditional systems, the couples span a similar range. Indeed, the high redox potential of the [Mn(II)(Me$_2$BBZ)Cl]Cl complex suggest that it could be used for catalytic epoxidations as has been demonstrated for the Mn(III) porphyrins and phthalocyanines.[72,73] This is indeed the case. We examined the [Mn(II)(Me$_2$BBZ)Cl]Cl mediated epoxidation of styrene in the presence of sodium hypochlorite, and the results from these experiments are given in Table 5. These data clearly demonstrate that [Mn(II)(Me$_2$BBZ)Cl]Cl is an epoxidation catalyst. Interestingly, in analogy to Mn(III)(salen), additives such as 4-phenyl-pyridine N-oxide (PPNO) were found to improve the yields significantly.[74]

A solution of styrene (0.085 g, 0.82 mmol), [Mn(Me$_2$BBZ)Cl]Cl.4H$_2$O (0.0057 g, 0.0085 mmol) was prepared in CH$_3$CN (5 mnL). A NaOCl solution (Fisher Chemicals, 4.57% as determined by iodometric titration) (1.31 mnL, 0.799 mmol) was syringed into the reaction mixture, and then the solution was stirred vigorously for 14 hours. The organic and aqueous layers were separated and the organic layer was dried with Na$_2$SO$_4$. The sample was analyzed by GC-MS using dodecane as an internal standard. Standardization curves for styrene, styrene oxide, and benzaldehyde were obtained using a similar protocol.

Control experiments were done in the absence of the [Mn(Me$_2$BBZ)Cl]Cl catalyst under identical conditions. For comparison, the epoxidation of styrene using MnCl$_2$.4H$_2$O (0.0017 g, 0.0085 mmol) and Jacobsen's catalyst, i.e. (R,R)-(−)N,N'-bis(3,5-di-t-butylsalicylidene)-1,2-cyclohexanediaminomanganese(III)chloride, (0.0054 g, 0.0085 mmol) as alternative catalytic mediators were performed under identical conditions. The effect of 4-phenylpyridine N-oxide (0.016 g, 0.0934 mmol) on the catalytic activity was also explored by adding it to the reaction mixture.

CONCLUSION

The four nitrogens of the Me$_2$BBZ ligand bind the metal in the equatorial plane, and like many porphyrins, the Me$_2$BBZ ligand exhibits non-planar distortions. Due to the geometric constraints of the phenyl-benzimidazole backbone, however, the type of perturbation exhibited by the Me$_2$BBZ ligand differs from the typical distortions observed for porphyrins. This new distortion mode is of interest, because, due to the lower symmetry of the ligand, it leads to two atropisomers, that when separated could find applications in asymmetric synthesis. Indeed, we show here that the manganese complex formed with this ligand, [Mn(Me$_2$BBZ)

Cl]Cl, can support catalytic epoxidation activity of styrene with reasonable activity. The diprotonated $Me_2BBZ$ ligand and $[Mn(Me_2BBZ)Cl]Cl$ complex, also exhibit optical and electrochemical properties distinct from their corresponding porphyrin and phthalocyanine analogs. These distinct properties suggest the possibility of new applications for the bis-benzimidazole macrocycle.

TABLE 1

Crystallographic Data for $[H_2(Me_2BBZ)](ClO_4)_2$ (8) and $[Mn(Me_2BBZ)Cl]Cl \cdot xH_2O$ (9).

|  | 8 | 9 |
|---|---|---|
| Formula | $C_{30}H_{24}Cl_2N_6O_8$ | $C_{30}H_{22}Cl_2MnN_6 + x(H_2O)$ |
| Formula weight | 667.45 | 592.38[a] |
| crystal system | monoclinic | Triclinic |
| space group | $P2_1/n$ | P1 bar |
| a, Å | 8.7086(2) | 8.1128(3) |
| b, Å | 28.8382(7) | 13.3182(6) |
| c, Å | 11.9403(3) | 14.3727(6) |
| α, deg | 90. | 67.527(1) |
| β, deg | 100.147(1) | 87.063(1) |
| γ, deg | 90. | 83.148(1) |
| Z, formula unit | 4 | 2 |
| V, Å$^3$ | 2951.8(1) | 1424.7(1) |
| $d_{calcd}$, g·cm$^{-1}$ | 1.50 | 1.38[a] |
| $\mu_{calcd}$, mm$^{-1}$ | 0.284 | 0.680[a] |
| no. of data collected | 18805 | 16307 |
| no. of unique data (all) | 6743 | 7290 |
| no. of variable parameters | 410 | 345 |
| $R_1$,[b] $wR_2$[c] (2σ) | 0.097, 0.216 | 0.0515, 0.1007 |
| $R_1$,[b] $wR_2$[c] (all data) | 0.169, 0.258 | 0.1283, 0.1203 |
| gof on F$^2$ (all data) | 1.039 | 0.899 |

[a] Based on the Mn complex only
[b] $R_1 = \Sigma\|F_O| - |F_C\|/\Sigma|F_O|$
[c] $wR_2(F^2) = [\Sigma w(F_O^2 - F_C^2)^2/\Sigma w(F_O^2)^2]^{1/2}$, $w = 1/[\sigma^2(F_O^2) + (0.0841P)^2 + 7.8966P]$, where $P = (F_O^2 + 2F_C^2)/3$ for 8, and $w = 1/[\sigma^2(F_O^2) + (0.0511P)^2 + 0.0000P]$, where $P = (F_O^2 + 2F_C^2)/3$ for 9.

TABLE 2

Selected Bond Distances (Å) and Angles (deg) for $[H_2(Me_2BBZ)](ClO_4)_2$ (8).

| | | | | | |
|---|---|---|---|---|---|
| N(1)-C(29) | 1.342(6) | N(6)-C(16) | 1.400(6) | C(13)-C(14) | 1.470(7) |
| N(1)-C(1) | 1.372(6) | N(6)-C(15) | 1.470(6) | C(16)-C(17) | 1.383(7) |
| N(2)-C(22) | 1.270(6) | C(1)-C(2) | 1.388(6) | C(16)-C(21) | 1.386(7) |
| N(2)-C(23) | 1.413(6) | C(1)-C(6) | 1.414(7) | C(17)-C(18) | 1.362(8) |
| N(3)-C(14) | 1.334(6) | C(2)-C(3) | 1.390(7) | C(18)-C(19) | 1.390(8) |
| N(3)-C(21) | 1.380(6) | C(3)-C(4) | 1.384(8) | C(19)-C(20) | 1.397(7) |
| N(4)-C(7) | 1.262(6) | C(4)-C(5) | 1.382(7) | C(20)-C(21) | 1.392(6) |
| N(4)-C(8) | 1.423(6) | C(5)-C(6) | 1.384(7) | C(20)-C(22) | 1.459(7) |
| N(5)-C(29) | 1.344(6) | C(6)-C(7) | 1.461(7) | C(23)-C(28) | 1.396(7) |
| N(5)-C(2) | 1.398(7) | C(8)-C(9) | 1.394(7) | C(23)-C(24) | 1.405(7) |
| N(5)-C(30) | 1.477(6) | C(8)-C(13) | 1.400(7) | C(27)-C(28) | 1.414(7) |
| N(6)-C(14) | 1.337(6) | C(12)-C(13) | 1.391(7) | C(28)-C(29) | 1.464(7) |
| C(29)-N(1)-C(1) | 110.1(4) | N(1)-C(1)-C(2) | 106.5(4) | | |
| C(22)-N(2)-C(23) | 118.8(4) | N(1)-C(1)-C(6) | 132.3(4) | | |
| C(14)-N(3)-C(21) | 110.3(4) | C(2)-C(1)-C(6) | 121.2(4) | | |
| C(7)-N(4)-C(8) | 118.8(4) | C(1)-C(2)-C(3) | 122.0(5) | | |
| C(29)-N(5)-C(2) | 108.7(4) | C(1)-C(2)-N(5) | 106.5(4) | | |
| C(29)-N(5)-C(30) | 127.9(5) | C(3)-C(2)-N(5) | 131.5(5) | | |
| C(2)-N(5)-C(30) | 123.1(5) | C(4)-C(3)-C(2) | 116.8(5) | | |
| C(14)-N(6)-C(16) | 108.7(4) | C(5)-C(4)-C(3) | 121.5(5) | | |
| C(14)-N(6)-C(15) | 127.8(4) | C(4)-C(5)-C(6) | 122.9(5) | | |
| C(16)-N(6)-C(15) | 123.2(4) | C(5)-C(6)-C(1) | 115.6(4) | | |
| C(5)-C(6)-C(7) | 121.7(5) | C(18)-C(19)-C(20) | 122.0(5) | | |
| C(1)-C(6)-C(7) | 122.6(4) | C(21)-C(20)-C(19) | 115.3(5) | | |
| N(4)-C(7)-C(6) | 120.7(4) | C(21)-C(20)-C(22) | 123.4(4) | | |
| C(9)-C(8)-C(13) | 119.0(4) | C(19)-C(20)-C(22) | 121.3(4) | | |
| C(9)-C(8)-N(4) | 121.3(5) | N(3)-C(21)-C(16) | 105.9(4) | | |
| C(13)-C(8)-N(4) | 119.7(4) | N(3)-C(21)-C(20) | 131.9(4) | | |
| C(12)-C(13)-C(8) | 119.8(5) | C(16)-C(21)-C(20) | 122.2(5) | | |
| C(12)-C(13)-C(14) | 120.5(5) | N(2)-C(22)-C(20) | 120.7(4) | | |
| C(8)-C(13)-C(14) | 119.7(4) | C(28)-C(23)-C(24) | 119.6(5) | | |
| N(3)-C(14)-N(6) | 108.4(4) | C(28)-C(23)-N(2) | 118.7(4) | | |
| N(3)-C(14)-C(13) | 124.9(4) | C(24)-C(23)-N(2) | 121.7(5) | | |
| N(6)-C(14)-C(13) | 126.7(4) | C(23)-C(28)-C(27) | 119.7(5) | | |
| C(17)-C(16)-C(21) | 121.4(5) | C(23)-C(28)-C(29) | 120.6(4) | | |
| C(17)-C(16)-N(6) | 132.0(5) | C(27)-C(28)-C(29) | 119.7(5) | | |
| C(21)-C(16)-N(6) | 106.6(4) | N(1)-C(29)-N(5) | 108.2(4) | | |
| C(18)-C(17)-C(16) | 117.3(5) | N(1)-C(29)-C(28) | 124.9(5) | | |

TABLE 2-continued

Selected Bond Distances (Å) and Angles (deg) for [H$_2$(Me$_2$BBZ)](ClO$_4$)$_2$ (8).

| C(17)-C(18)-C(19) | 121.7(5) | N(5)-C(29)-C(28) | 126.9(4) |

TABLE 3

Selected Bond Distances (Å) and Angles (deg) for [Mn(Me$_2$BBZ)Cl]Cl.xH$_2$O (9).

| | | | | | |
|---|---|---|---|---|---|
| Mn—N(3) | 2.118(2) | Mn—N(2) | 2.257(2) | Mn—Cl(1) | 2.3186(10) |
| Mn—N(1) | 2.127(2) | Mn—N(4) | 2.277(2) | | |
| N(1)-C(29) | 1.339(3) | N(6)-C(16) | 1.385(3) | C(13)-C(14) | 1.479(4) |
| N(1)-C(1) | 1.385(3) | N(6)-C(15) | 1.458(3) | C(16)-C(21) | 1.385(4) |
| N(2)-C(22) | 1.289(3) | C(1)-C(2) | 1.391(4) | C(16)-C(17) | 1.395(4) |
| N(2)-C(23) | 1.433(3) | C(1)-C(6) | 1.412(4) | C(17)-C(18) | 1.377(4) |
| N(3)-C(14) | 1.342(3) | C(2)-C(3) | 1.395(4) | C(18)-C(19) | 1.382(4) |
| N(3)-C(21) | 1.388(3) | C(3)-C(4) | 1.371(4) | C(19)-C(20) | 1.404(4) |
| N(4)-C(7) | 1.280(3) | C(4)-C(5) | 1.393(4) | C(20)-C(21) | 1.404(4) |
| N(4)-C(8) | 1.438(3) | C(5)-C(6) | 1.397(4) | C(20)-C(22) | 1.454(4) |
| N(5)-C(29) | 1.365(3) | C(6)-C(7) | 1.459(4) | C(23)-C(24) | 1.386(4) |
| N(5)-C(2) | 1.392(3) | C(8)-C(9) | 1.389(4) | C(23)-C(28) | 1.407(4) |
| N(5)-C(30) | 1.466(3) | C(8)-C(13) | 1.412(4) | C(27)-C(28) | 1.394(4) |
| N(6)-C(14) | 1.367(3) | C(12)-C(13) | 1.376(4) | C(28)-C(29) | 1.477(4) |
| N(3)-Mn—N(1) | 128.88(9) | N(2)-Mn—N(4) | 145.30(9) | | |
| N(3)-Mn—N(2) | 84.81(8) | N(3)-Mn—Cl(1) | 117.68(7) | | |
| N(1)-Mn—N(2) | 80.55(8) | N(1)-Mn—Cl(1) | 113.38(6) | | |
| N(3)-Mn—N(4) | 79.65(8) | N(2)-Mn—Cl(1) | 109.65(7) | | |
| N(1)-Mn—N(4) | 85.39(8) | N(4)-Mn—Cl(1) | 105.05(6) | | |
| C(29)-N(1)-C(1) | 106.2(2) | N(5)-C(2)-C(3) | 131.5(3) | | |
| C(29)-N(1)-Mn | 127.7(2) | C(4)-C(3)-C(2) | 116.4(3) | | |
| C(1)-N(1)-Mn | 125.8(2) | C(3)-C(4)-C(5) | 122.4(3) | | |
| C(22)-N(2)-C(23) | 116.3(2) | C(4)-C(5)-C(6) | 121.6(3) | | |
| C(22)-N(2)-Mn | 130.1(2) | C(5)-C(6)-C(1) | 116.3(3) | | |
| C(23)-N(2)-Mn | 113.5(2) | C(5)-C(6)-C(7) | 119.1(3) | | |
| C(14)-N(3)-C(21) | 105.7(2) | C(1)-C(6)-C(7) | 124.5(2) | | |
| C(14)-N(3)-Mn | 127.4(2) | N(4)-C(7)-C(6) | 124.4(3) | | |
| C(21)-N(3)-Mn | 126.9(2) | C(9)-C(8)-C(13) | 119.6(3) | | |
| C(7)-N(4)-C(8) | 118.0(2) | C(9)-C(8)-N(4) | 119.2(3) | | |
| C(7)-N(4)-Mn | 129.6(2) | C(13)-C(8)-N(4) | 121.1(2) | | |
| C(8)-N(4)-Mn | 112.2(2) | C(12)-C(13)-C(8) | 118.7(3) | | |
| C(29)-N(5)-C(2) | 107.3(2) | C(12)-C(13)-C(14) | 120.2(3) | | |
| C(29)-N(5)-C(30) | 129.5(2) | C(8)-C(13)-C(14) | 121.1(2) | | |
| C(2)-N(5)-C(30) | 122.9(2) | N(3)-C(14)-N(6) | 111.3(2) | | |
| C(14)-N(6)-C(16) | 107.1(2) | N(3)-C(14)-C(13) | 122.5(2) | | |
| C(14)-N(6)-C(15) | 129.0(2) | N(6)-C(14)-C(13) | 126.0(2) | | |
| C(16)-N(6)-C(15) | 123.6(2) | C(21)-C(16)-N(6) | 106.3(2) | | |
| N(1)-C(1)-C(2) | 109.4(2) | C(21)-C(16)-C(17) | 122.0(3) | | |
| N(1)-C(1)-C(6) | 130.0(2) | N(6)-C(16)-C(17) | 131.7(3) | | |
| C(2)-C(1)-C(6) | 120.6(2) | C(18)-C(17)-C(16) | 117.1(3) | | |
| C(1)-C(2)-N(5) | 105.9(2) | C(17)-C(18)-C(19) | 121.7(3) | | |
| C(1)-C(2)-C(3) | 122.6(3) | C(18)-C(19)-C(20) | 121.8(3) | | |
| C(19)-C(20)-C(21) | 116.3(3) | C(24)-C(23)-N(2) | 119.2(2) | | |
| C(19)-C(20)-C(22) | 119.5(3) | C(28)-C(23)-N(2) | 121.3(2) | | |
| C(21)-C(20)-C(22) | 124.1(2) | C(27)-C(28)-C(23) | 117.8(3) | | |
| C(16)-C(21)-N(3) | 109.5(2) | C(27)-C(28)-C(29) | 120.3(2) | | |
| C(16)-C(21)-C(20) | 121.0(2) | C(23)-C(28)-C(29) | 121.8(2) | | |
| N(3)-C(21)-C(20) | 129.5(2) | N(1)-C(29)-N(5) | 111.3(2) | | |
| N(2)-C(22)-C(20) | 124.5(2) | N(1)-C(29)-C(28) | 123.0(2) | | |
| C(24)-C(23)-C(28) | 119.5(3) | N(5)-C(29)-C(28) | 125.7(2) | | |

TABLE 4

Comparison of the displacements of the C$_m$ and C$_b$ atoms in representative nonplanar porphyrins and the displacements of the corresponding atoms in the two bis-benzimidazole structures.

| Compound | Distortion Mode | Average absolute displacement C$_m$[a] | Average absolute displacement C$_b$[a] | Reference |
|---|---|---|---|---|
| [H$_2$(Me$_2$BBZ)](ClO$_4$)$_2$ | twist | 93 | 136 | |
| [Mn(Me$_2$BBZ)Cl]Cl | twist | 77 | 110 | |
| Mn(TPP) (1-MeIm)][b] | dom | 5 | 18 | 63 |
| [Mn(TPP) (Py)Cl][b] | ruf | 30 | 26 | 81 |
| [Mn(TPP) (2,6-LutNO)$_2$]ClO$_4$[b] | ruf | 44 | 17 | 82 |
| Mn(TPP) (NO)[c] | sad | 16 | 35 | 83 |

TABLE 4-continued

Comparison of the displacements of the $C_m$ and $C_b$ atoms in representative nonplanar porphyrins and the displacements of the corresponding atoms in the two bis-benzimidazole structures.

| Compound | Distortion Mode | Average absolute displacement $C_m{}^a$ | $C_b{}^a$ | Reference |
|---|---|---|---|---|
| $H_4TPP^{2+b}$ | sad | 6 | 90 | 84 |

[a] Value in Å × $10^2$.
[b] TPP - dianion of 5, 10, 15, 20-tetraphenylporphyrin, 1-MeIm - 1-methylimidazole, 2,6-LutNO - 2,6-dimethylpyridine-N-oxide.
[c] TTP - dianion of 5, 10, 15, 20-tetra-p-tolylporphyrin.

TABLE 5

[$Mn(Me_2BBZ)Cl$]Cl catalyzed epoxidation of styrene using NaOCl oxidant

| Catalyst | Styrene Oxide | Benzaldehyde | Turnover Number[a] |
|---|---|---|---|
| [$Mn(Me_2BBZ)Cl$]Cl | 56% | 5.8% | 53 |
| [$Mn(Me_2BBZ)Cl$]Cl + PPNO[b] | 73% | 11% | 70 |
| $MnCl_2 \cdot 4H_2O$ | 9.1% | 10% | 8.6 |
| None | 9.5% | 11% | |
| Jacobsen's catalyst | 72% | 4.5% | 69 |

[a] Based on yield of styrene oxide.
[b] PPNO - 4-phenyl-pyridine N-oxide.

REFERENCES

1) Gong, W.; Hao, B.; Mansy, S. S.; Gonzalez, G.; Gilles-Gonzalez, M. A.; Chan, M. K. *Proc. Natl. Acad. Sci. U.S.A.* 1998, 95, 15177–15182.
2) Gilles-Gonzalez, M. A.; Ditta, G.; Helinski, D. R. *Nature* 1991, 350, 170–172.
3) Gilles-Gonzalez, M. A.; Gonzalez, G.; Perutz, M. F.; Kiger, L.; Marden, M.; Poyart, C. *Biochemistry* 1994, 33, 8067–8073.
4) Shelver, D.; Kerby, R. L.; He, Y.; Roberts, G. P. *Proc. Natl. Acad. Sci. USA* 1997, 94, 11216–11220.
5) Garbers, D. L.; Lowe, D. G. *J. Biol. Chem.* 1994, 269, 30741–30744.
6) Perutz, M. F. *Nature* 1970, 228, 726–739.
7) Weichsel, A.; Anderson, J. F.; Champagne, D. E.; Walker, F. A.; Montfort, W. R. *Nature Struct. Biol.* 1998, 5, 304–309.
8) Ludwig, M. L.; Matthews, R. G. *Annu. Rev. Biochem.* 1997, 66, 269–313.
9) Ludwig, M. L.; Drennan, C. L.; Matthews, R. G. *Structure (London)* 1996, 4, 505–512.
10) Drennan, C. L.; Matthews, R. G.; Ludwig, M. L. *Curr. Opin. Struct. Biol.* 1994, 4, 919–29.
11) Drennan, C. L.; Huang, S.; Drummond, J. T.; Matthews, R. G.; Ludwig, M. *Science* (Washington, D.C.) 1994, 266, 1669–74.
12) Furenlid, L. R.; Renner, M. W.; Fajer, J. *J. Am. Chem. Soc.* 1990, 112, 8987–8989.
13) Ermler, U.; Grabarse, W.; Shima, S.; Goubeaud, M.; Thauer, R. K. *Science* 1997, 278, 1413–1415.
14) Sono, M.; Roach, M. P.; Coulter, B. D.; Dawson, J. H. *Chem. Rev.* 1996, 96, 2841–88.
15) Groves, J. T.; Myers, R. S. *J. Am. Chem. Soc.* 1983, 105, 5791–5796.
16) Collman, J. P.; Zhang, X.; Lee, V. J.; Uffelman, E. S.; Brauman, J. I. *Science* 1993, 261, 1404–1411.
17) Groves, J. T.; Viski, P. *J. Am. Chem. Soc.* 1989, 111, 8537–8538.
18) Groves, J. T.; Viski, P. *J. Org. Chem.* 1990, 55, 3628–3634.
19) Groves, J. T.; Takahashi, T. *J. Am. Chem. Soc.* 1983, 105, 2073–4.
20) Moser, F. H.; Thomas, A. L. *The Phthalocyanines:Manufacture and Applications*; CRC Press, Inc: Boca Raton, Fla., 1983; Vol. 2.
21) Akerfeldt, K. S.; Kim, R. M.; Camac, D.; Groves, J. T.; Lear, J. D.; DeGrado, W. F. *J. Am. Chem. Soc.* 1992, 114, 9656–9657.
22) Drain, C. M.; Nifiatis, F.; Vasenko, A.; Batteas, J. D. *Angew. Chem., Int. Ed.* 1998, 37, 2344–2347.
23) Sessler, J. L. *Expanded, contracted & isomeric porphyrins*; Pergamon: Oxford, U.K., 1997; Vol. 15.
24) Gale, P. A.; Sessler, J. L.; Král, V. *Chem. Comm.* 1998, 1–8.
25) Velazquez, C. S.; Broderick, W. E.; Sabat, M.; Barrett, A. G. M.; Hoffman, B. M. *J. Am. Chem. Soc.* 1990, 112, 7408–7410.
26) Strachan, J.-P.; Gentemann, S.; Seth, J.; Kalsbeck, W. A.; Lindsey, J. S.; Holten, D.; Bocian, D. F. *J. Am. Chem. Soc.* 1997, 119, 11191–11201.
27) Drain, C. M.; Lehn, J.-M. *J. Chem. Soc., Chem. Commun.* 1994, 2313–2315.
28) Furenlid, L. R.; Renner, M. W.; Smith, K. M.; Fajer, J. *J. Am. Chem. Soc.* 1990, 112, 1634–1635.
29) Deisenhofer, J.; Michel, H. *Angew. Chem. Int. Ed. Engl.* 1989, 28, 829–47.
30) Deisenhofer, J.; Michel, H. *Science* 1989, 245, 1463–1473.
31) Geno, M. K.; Halpern, J. *J. Am. Chem. Soc.* 1987, 109, 1238–1240.
32) Jentzen, W.; Song, X.-Z.; Shelnutt, J. A. *J. Phys. Chem. B* 1997, 101, 1684–1699.
33) Hobbs, J. D.; Shelnutt, J. A. *J. Protein Chem.* 1995, 14, 19–25.
34) Wolowiec, S.; Latos-Grazynski, L.; Toronto, D.; Marchon, J.-C. *Inorg. Chem.* 1998, 37, 724–732.
35) Drain, C. M.; Gentemann, S.; Roberts, J. A.; Nelson, N. Y.; Medforth, C. J.; Jia, S.; Simpson, M. C.; Smith, K. M.; Fajer, J.; Shelnutt, J. A.; Holten, D. *J. Am. Chem. Soc.* 1998, 120, 3781–3791.
36) Medforth, C. J.; Senge, M. O.; Smith, K. M.; Sparks, L. D.; Shelnutt, J. A. *J. Am. Chem. Soc.* 1992, 114, 9859–9869.
37) Regev, A.; Galili, T.; Medforth, C. J.; Smith, K. M.; Barkigia, K. M.; Fajer, J.; Levanon, H. *J. Phys. Chem.* 1994, 98, 2520–2526.
38) Nurco, D. J.; Medforth, C. J.; Forsyth, T. P.; Olmstead, M. M.; Smith, K. M. *J. Am. Chem. Soc.* 1996, 118, 10918–10919.
39) Song, X.-Z.; Jentzen, W.; Jaquinod, L.; Khoury, R. G.; Medforth, C. J.; Jia, S.-L.; Ma, J.-G.; Smith, K. M.; Shelnutt, J. A. *Inorg. Chem.* 1998, 37, 2117–2128.
40) Jentzen, W.; Simpson, M. C.; Hobbs, J. D.; Song, X.; Ema, T.; Nelson, N. Y.; Medforth, C. H.; Smith, K. M.; Verat, M.; Mazzanti, M.; Ramasseul, N. Y.; Marchon, J.-C.; Takeuchi, T.; Goddard, W. A.; Shelnutt, J. A. *J Am. Chem. Soc.* 1995, 117, 11085–11097.
41) Song, X.-Z.; Jentzen, W.; Jia, S.-L.; Jaquinod, L.; Nurco, D. J.; Medforth, C. J.; Smith, K. M.; Shelnutt, J. A. *J. Am. Chem. Soc.* 1996, 118, 12975–12988.
42) Shelnutt, J. A.; Medforth, C. J.; Berber, M. D.; Barkigia, K. M.; Smith, K. M. *J. Am. Chem. Soc.* 1991, 113, 4077–4087.

43) Gentemann, S.; Nelson, N. Y.; Jaquinod, L.; Nurco, D. J.; Leung, S. H.; Medforth, C. J.; Smith, K. M.; Fajer, J.; Holten, D. *J. Phys. Chem.* B 1997, 101, 1247–1254.

44) Gentemann, S.; Medforth, C. J.; Forsyth, T. P.; Nurco, D. J.; Smith, K. M.; Fajer, J.; Holten, D. *J. Am. Chem. Soc.* 1994, 116, 7363–7368.

45) Gentemann, S.; Medforth, C. J.; Ema, T.; Nelson, N. Y.; Smith, K. M.; Fajer, J.; Holten, D. *Chem. Phys. Lett.* 1995, 245, 441–447.

46) Charlesworth, P.; Truscott, T. G.; Kessel, D.; Medforth, C. J.; Smith, K. M. *J. Chem. Soc., Faraday Trans.* 1994, 90, 1073–1076.

47) Lin, C.-Y.; Hu, S.; Rush, T. I.; Spiro, T. G. *J. Am. Chem. Soc.* 1996, 118, 9452–9453.

48) Takeda, J.; Sato, M. *Chem. Lett.* 1995, 939–940.

49) Tsuchiya, S. *Chem. Phys. Lett.* 1990, 169, 608–610.

50) Ravikanth, M.; Reddy, D.; Chandrashekar, T. K. *J. Photochem. Photobiol. A: Chem* 1993, 72, 61–67.

51) Drain, C. M.; Kirmaier, C.; Medforth, C. J.; Nurco, D. J.; Smith, K. M.; Holten, D. *J. Phys. Chem.* 1996,100, 11984–11993.

52) Preston, P. N. Benzimidazoles; Preston, P. N., Ed.; John Wiley and Sons:New York, 1981; Vol. 40,pp 1–285.

53) Hendrickson, J. B.; Hussoin, M. S. *J. Org. Chem.* 1989, 54, 1144–1149.

54) Wang, H.; Partch, R. E.; Li, Y. *J. Org. Chem.* 1997, 62, 5222–5225.

55) Jonas, R.; Klockow, M.; Lues, I.; Prücher, H.; Schliep, H. J.; Wurziger, H. Eur. *J. Med. Chem* 1993,28, 129–140.

56) Jonas, R.; Prücher, H.; Wurziger, H. Eur. *J. Med. Chem.* 1993, 28, 141–148.

57) Gonzalez, B.; Kouba, J.; Yee, S.; Reed, C. A.; Kirner, J. F.; Scheidt, R. *J. Am. Chem. Soc.* 1975, 97, 3247–3249.

58) VanAtta, R. B.; Strouse, C. E.; Hanson, L. K.; Valentine, J. S. *J. Am. Chem. Soc.* 1987, 1987, 1425–1434.

59) Kirner, J. F.; Dow, W.; Scheidt, W. R. *Inorg Chem.* 1976,15, 1685–1690.

60) Mason, R.; Williams, G. A. *J. C.S. Dalton* 1979, 676–683.

61) Munro, O. Q.; Bradley, J. C.; Hancock, R. D.; Marques, H. M.; Marsicano, F.; Wade, P. W. *J. Am. Chem. Soc.* 1992, 114, 7218–7230.

62) Scheidt, W. R.; Lee, Y. *J. Struct. Bonding* 1987, 64, 1–70.

63) Kirner, J. F.; Reed, C. A.; Scheidt, W. R. *J. Am. Chem. Soc.* 1977, 99, 2557–2563.

64) Falk, J. E. *Porphyrins and Metalloporphyrins: Their General, Physical and Coordination Chemistry, and Laboratory Methods*; Elsevier Publishing Company: Amsterdam, 1964.

65) Gouterman, M. *Optical Spectra and Electronic Structure*; Gouterman, M., Ed.; Academic Press: New York, 1977; Vol. III, Part A, pp 1–165.

66) Loew, G. H. *Theoretical Investigations of Iron Porphyrins*; Loew, G. H., Ed.; Addison-Wesley Publishing Company:Reading, Mass., 1983,pp 1–87.

67) Moser, F. H.; Thomas, A. L. *The Phthalocyanines: Properties*; CRC Press, Inc.: Boca Raton, Fla., 1983; Vol. 1.

68) McKeown, N. B. *Phthalocyanine Materials*; Cambridge University Press: Cambridge, 1998.

69) Guilard, R.; Perie, K.; Barbe, J.-M.; Nurco, D. J.; Smith, K. M.; Caemelbecke, E. V.; Kadish, K. M. *Inorg. Chem.* 1998, 37, 973–981.

70) Jeon, S.; Bruice, T. C. *Inorg. Chem.* 1992, 31, 4843–4848.

71) Lever, A. B. P.; Minor, P. C.; Wilshire, J. P. *Inorg. Chem.* 1981, 20, 2550–2553.

72) Creager, S. E.; Raybuck, S. A.; Murray, R. W. *J. Am. Chem. Soc.* 1986, 108, 4225–4227.

73) Larsen, E.; Jorgensen, K. A. *Acta Chem. Scand.* 1989, 43, 259–263.

74) Katsuki, T. *Journal of Molecular Catalysis A: Chemical* 1996, 113, 87–107.

75) Sheldrick, G. M. "SADABS," University of Göttingen, 1997.

76) Sheldrick, G. M. *Acta Crystallogr.* 1990, A46, 467–473.

77) Sheldrick, G. M. "SHELXL-93, Program for the Refinement of Crystal Structures," University of Göttingen, 1993.

78) *International Tables for Crystallography*; Kluwer Academic Publishers: Dordrecht, The Netherlands, 1992; Vol. C.

79) van der Sluis, P.; Spek, A. L. *Acta Cryst.* 1990, A46, 194–201.

80) Spek, A. L. *Acta Cryst.* 1990, A46, C-34.

81) Kirner, J. F.; Scheidt, W. R. *Inorg. Chem.* 1975,14, 2081–2086.

82) Hill, C. L.; Williamson, M. M. *Inorg. Chem.* 1985, 24, 3024–3030.

83) Scheidt, W. R.; Hatano, K.; Rupprecht, G. A.; Piciulo, P. L. *Inorg. Chem.* 1979, 18, 292–299.

84) Navaza, A.; de Rango, C.; Charpin, P. *Acta Crystallogr.* 1983, C39, 1625–1628.

We claim:

1. A ligand of the formula wherein
$R_1$ and $R_2$ may be the same or different and are selected from H, an alkyl having 1 to 10 carbon atoms, a benzyl group, a substituted 2-ethylphenyl group, a carbonyl group, a phenyl substituent, a tosyl group, and an alkylsulfonate group;

$R_3$ and $R_4$ may be the same or different and are selected from H, methyl, and ethyl; and $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$ and $R_{18}$ may be the same or different and are selected from H, alkyl having 1 to 10 carbon atoms, fluoride, chloride, bromide, iodide, nitro, amino, a carboxylate, an ester, and a phenyl group.

2. A complex chemical compound comprising a cation, wherein the cation is hydrogen or a transition metal, and at least one ligand of the formula of claim 1.

3. The complex of claim 2, wherein the complex contains manganese.

4. The ligand of claim 1, wherein the ligand is protonated.

5. The complex of claim 2, wherein the complex contains a transition metal.

6. A complex chemical compound composed of a ligand and at least one cation, wherein the ligand is a cyclic bis-benzimidazole.

7. A composition comprising a polar solvent having the ligand of claim 1 dissolved therein.

8. The composition of claim 7 further comprising ions of a transition metal dissolved in the polar solvent.

9. The composition of claim 8, further comprising an acid dissolved in the polar solvent.

10. A process for forming a complex containing a cyclic bis benzimidazole ligand comprising contacting a benzimidazole compound selected from the group consisting of a (2-aminophenyl)-benzimidazole-4-carboxaldehyde acetal and a (2-nitrophenyl)-benzimidazole-4-benzaldehyde with an acid optionally in the presence of a metal or a metal salt until the ligand is formed.

11. The process of claim 10, wherein the benzimidazole compound is a (2-aminophenyl)-benzimidazole-4-carboxaldehyde alkyl acetal in which the alkyl group has 1 to 10 carbon atoms.

12. The process of claim 10, wherein the benzimidazole compound is a (2-aminophenyl)-benzimidazole-4-carboxaldehyde ethyl acetal.

13. The process of claim 10, wherein the benzimidazole compound is a (2-nitrophenyl)-benzimidazole-4-benzaldehyde.

14. The process of claim 10, wherein cyclization is carried out in a polar solvent.

15. The process of claim 10, wherein cyclization is carried out in the presence of a divalent metal.

16. The process of claim 10, wherein cyclization is carried out in the presence of a transition metal.

17. The process of claim 10, wherein cyclization is carried out in the presence of iron or manganese.

18. A process for forming a transition metal complex compound comprising contacting the protonated cyclic bis benzimidazole ligand of claim 4 with a transition metal dissolved in a polar solvent.

19. The process of claim 18, wherein the process is carried out under oxidizing conditions.

20. A ligand of the formula

[chemical structure]

wherein $R_1$ and $R_2$ may be the same or different and are selected from H, an alkyl having 1 to 10 carbon atoms, a benzyl group, a substituted 2-ethylphenyl group, a carbonyl group, a phenyl substituent, a tosyl group, an alkylsulfonate group and a methyl-2-pyrrolidine methyl group;

$R_3$ and $R_4$ may be the same or different and are selected from H, methyl, and ethyl; and $R_5, R_6, R_7, R_8, R_9, R_{10}, R_{11}, R_{12}, R_{13}, R_{14}, R_{15}, R_{16}, R_{17}$, and $R_{18}$ may be the same or different and are selected from H, alkyl having 1 to 10 carbon atoms, fluoride, chloride, bromide, iodide, nitro, amino, a carboxylate, an ester, and a phenyl group.

21. A complex chemical compound comprising a cation, wherein the cation is hydrogen or a metal and at least one ligand represented by the following formula

[chemical structure] MX wherein $R_1$ and $R_2$ may be the same or different and are selected from H, an alkyl having 1 to 10 carbon atoms, a benzyl group, a substituted 2-ethylphenyl group, a carbonyl group, a phenyl substituent, a tosyl group, an alkylsulfonate group and a methyl-2-pyrrolidene methyl group;

$R_3$ and $R_4$ may be the same or different and are selected from H, methyl, and ethyl;

$R_5, R_6, R_7, R_8, R_9, R_{10}, R_{11}, R_{12}, R_{13}, R_{14}, R_{15}, R_{16}, R_{17}$, and $R_{18}$ may be the same or different and are selected from H, alkyl having 1 to 10 carbon atoms, fluoride, chloride, bromide, iodide, nitro, amino, a carboxylate, an ester, and a phenyl group;

M represents a counter-cation selected from the group consisting of hydrogen and metals from Groups IA and IIA of the Periodic Table, the transition metals, silicon and lead; and X represents a counter-anion.

22. The compound of claim 21, wherein the counter-anion is selected from the group consisting of halide ions, perchlorate, tetraphenyl boride ($Ph_4B^-$), sulfate, phosphate, carbonate, bicarbonate, tetrafluoroboride ($BF_4^-$) and hexafluorophosphide ($BF_6^-$).

23. The compound of claim 22, wherein M is selected from the group consisting of H, Mn, Fe, Co, Ni and Cu.

24. The compound of claim 23, wherein X is selected from halide, perchlorate, tetraphenyl boride ($Ph_4B^-$) and tetrafluoroboride ($BF_4^-$).

25. The compound of claim 24, wherein M is a transition metal and X is chloride.

26. The compound of claim 22, wherein X is selected from halide, perchlorate, tetraphenyl boride ($Ph_4B^-$) and tetrafluoroboride ($BF_4^-$).

27. The compound of claim 26, wherein M is a transition metal and X is chloride.

* * * * *